United States Patent
Nie et al.

(10) Patent No.: US 12,315,084 B2
(45) Date of Patent: *May 27, 2025

(54) SYSTEM AND METHOD FOR EXTRACTING A REGION OF INTEREST FROM VOLUME DATA

(71) Applicant: SHANGHAI UNITED IMAGING HEALTHCARE CO., LTD., Shanghai (CN)

(72) Inventors: Weipin Nie, Shanghai (CN); Yue Gao, Shanghai (CN); Hao Zeng, Shanghai (CN); Chao Fu, Shanghai (CN); Ce Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/477,535

(22) Filed: Sep. 28, 2023

(65) Prior Publication Data
US 2024/0029359 A1 Jan. 25, 2024

Related U.S. Application Data

(63) Continuation of application No. 17/305,248, filed on Jul. 2, 2021, now Pat. No. 11,776,216, which is a
(Continued)

(51) Int. Cl.
*G06T 19/00* (2011.01)
*G06T 7/11* (2017.01)
(Continued)

(52) U.S. Cl.
CPC ............... *G06T 19/00* (2013.01); *G06T 7/11* (2017.01); *G06T 7/12* (2017.01); *G06T 7/187* (2017.01);
(Continued)

(58) Field of Classification Search
CPC .... G06V 10/25; G06V 2201/031; G06T 7/12; G06T 7/11; G06T 7/187; G06T 19/00;
(Continued)

(56) References Cited

U.S. PATENT DOCUMENTS

| | | | |
|---|---|---|---|
| 6,754,374 B1* | 6/2004 | Miller | ............... G06T 7/187 382/128 |
| 6,898,263 B2 | 5/2005 | Avinash et al. | |

(Continued)

FOREIGN PATENT DOCUMENTS

| | | |
|---|---|---|
| CN | 1943512 A | 4/2007 |
| CN | 102622750 A | 8/2012 |
| CN | 104850219 A | 8/2015 |

OTHER PUBLICATIONS

Sekiguchi, Hiroyuki, Koichi Sano, and Tetsuo Yokoyama. "Interactive 3-dimensional segmentation method based on region growing method." Systems and Computers in Japan 25.1 (1994): 88-97. (Year: 1994).*

(Continued)

*Primary Examiner* — Vu Le
*Assistant Examiner* — Tracy Mangialaschi
(74) *Attorney, Agent, or Firm* — METIS IP LLC

(57) ABSTRACT

The present disclosure relates to a system and method for extracting a region of interest. Image data in a first sectional plane may be acquired. The image data in the first sectional plane may include at least one first slice image and one second slice image. A first region of interest (ROI) in the first slice image may be determined. A second ROI in the second slice image may be determined. A first volume of interest (VOI) may be determined based on the first ROI, the second ROI, and characteristic information of the image data in the first sectional plane.

6 Claims, 13 Drawing Sheets

Related U.S. Application Data continuation of application No. 16/236,622, filed on Dec. 30, 2018, now Pat. No. 11,094,066, which is a continuation of application No. PCT/CN2017/095320, filed on Jul. 31, 2017.

(51) Int. Cl.
  *G06T 7/12* (2017.01)
  *G06T 7/187* (2017.01)
  *G06T 19/20* (2011.01)
  *G06V 10/25* (2022.01)

(52) U.S. Cl.
  CPC .............. *G06T 19/20* (2013.01); *G06V 10/25* (2022.01); *G06T 2207/20104* (2013.01); *G06T 2207/30056* (2013.01); *G06T 2207/30096* (2013.01); *G06T 2207/30101* (2013.01); *G06T 2210/41* (2013.01); *G06T 2219/028* (2013.01); *G06T 2219/2021* (2013.01); *G06V 2201/031* (2022.01)

(58) Field of Classification Search
  CPC ........... G06T 19/20; G06T 2207/30101; G06T 2207/20104; G06T 2207/30096; G06T 2207/30056; G06T 2210/41; G06T 2219/028; G06T 2219/2021; G16H 30/40; G16H 30/20; G16H 501/20; A61B 2034/105; A61B 2034/107; A61B 2576/00
  See application file for complete search history.

(56) References Cited

U.S. PATENT DOCUMENTS

| | | | |
|---|---|---|---|
| 8,155,405 | B2 | 4/2012 | Unal et al. |
| 2004/0249270 | A1 | 12/2004 | Kondo et al. |
| 2008/0123914 | A1 | 5/2008 | De Bliek et al. |
| 2008/0137926 | A1 | 6/2008 | Skinner et al. |
| 2008/0260221 | A1 | 10/2008 | Unal et al. |
| 2009/0322748 | A1* | 12/2009 | Chen .................. G06T 7/11 345/424 |
| 2010/0265251 | A1* | 10/2010 | Vining ................ G06T 5/00 345/420 |
| 2012/0192401 | A1 | 8/2012 | Pavlovskaia et al. |
| 2013/0169639 | A1* | 7/2013 | Shi ..................... G06T 7/11 345/424 |
| 2014/0147025 | A1 | 5/2014 | Periaswamy et al. |
| 2017/0337687 | A1 | 11/2017 | Wang et al. |
| 2018/0189953 | A1 | 7/2018 | Nie et al. |

OTHER PUBLICATIONS

Peng, Ruiyun et al., Serial slice image preprocessing, 3D reconstruction and stereological analysis, Morphometrics and Image Analysis, 2012, 12 pages.

Hiroyuki Sekiguchi et al., Interactive 3-Dimensional Segmentation Method Based on Region Growing Method, Systems and Computers in Japan, 25(1): 88-97, 1994.

International Search Report in PCT/CN2017/095320 mailed on May 8, 2018, 7 pages.

Written Opinion in PCT/CN2017/095320 mailed on May 8, 2018, 8 pages.

Partial Supplementary European Search Report in European Application No. 17919848.6 mailed on Jun. 24, 2020, 12 pages.

The Extended European Search Report in European Application No. 17919848.6 mailed on Oct. 6, 2020, 20 pages.

Markus Hadwiger et al., Interactive Volume Exploration for Feature Detection and Quantification in Industrial CT Data, IEEE Transactions on Visualization and Computer Graphics, 14(6): 1507-1514, 2008.

David Shattuck, BrainSuite GUI: Surface Extraction and Visualization, 2017 BrainSuite Training Workshop, 2017, 53 pages.

Akshat Gotra et al., Liver Segmentation: Indications, Techniques and Future Directions, Insights Imaging, 8(4): 377-392, 2017.

Laszlo Rusko et al., Virtual Volume Resection Using Multi-resolution Triangular Representation of B-spline Surfaces, Computer Methods And Programs in Biomedicine, 111(2): 315-329, 2013.

Runzhen Huang et al., RGVis: Region Growing Based Techniques for Volume Visualization, Proceedings of The 11th Pacific Conference on Computer Graphics & Applications, 2003, 9 pages.

Hung-Li Jason Chen et al., GPU-based Point Radiation for Interactive Volume Sculpting and Segmentation, The Visual Computer, 24(7-9): 689-698, 2008.

Orazio Gambino et al., Automatic Volumetric Liver Segmentation Using Texture Based Region Growing, 2010 International Conference on Complex, Intelligent and Software Intensive Systems, 2010, 7 pages.

\* cited by examiner

SYSTEM AND METHOD FOR EXTRACTING A REGION OF INTEREST FROM VOLUME DATA

CROSS-REFERENCE TO RELATED APPLICATIONS

This present application is a continuation of U.S. application Ser. No. 17/305,248, filed on Jul. 2, 2021, which is a continuation of U.S. application Ser. No. 16/236,622 (now issued as U.S. Ser. No. 11/094,066B2), filed on Dec. 30, 2018, which is a continuation of International Application No. PCT/CN2017/095320, filed on Jul. 31, 2017, the contents of each of which are hereby incorporated by reference in its entirety.

TECHNICAL FIELD

The present disclosure generally relates to a system and method for image processing, and more specifically, relates to an interactive system and method for extracting a region of interest from volume data.

BACKGROUND

With the development of science and technology, medical images are widely used in clinical detection and diagnosis. Medical images of high quality contribute to accurately locating lesions and help improve the accuracy of diagnosis. During a process of detection and diagnosis (e.g., segmentation of a liver, detection of a tumor, a surgical analysis, etc.), usually tissue may need to be marked in images, gray level information of a volume of interest (VOI) may be extracted, and information relating to the tissue and/or VOI may be displayed on a three-dimensional image for observation. Currently, a commonly used method is to draw a contour outline of a regions of interest (ROI) on a two-dimensional image, expand the ROI to a three-dimensional VOI according to the contour outline, and then display the results. Existing methods do not allow editing the VOI directly on a three-dimensional image or allow a user to directly understand the effect on the whole extraction process of the VOI caused by the drawing of the contour outlines of ROIs in different slices. Therefore, it may be difficult for the generated VOI to be satisfactory to a user.

Furthermore, during the process of extracting an ROI, a region growing algorithm is commonly used to perform image segmentation. In a three-dimensional image, a spatial relationship is present between different tissues. When region growing is performed on tissue (e.g., blood vessel(s)), real-time results may be masked by other tissue (e.g., skeleton(s)), which can make it inconvenient for a user to observe. Hence, the present disclosure provides a method that can facilitate a user to interact with an image processing system. The method can enable a user to observe and/or adjust the real-time extraction result(s) conveniently during a full-automatic, semi-automatic or manual extraction of an ROI.

SUMMARY

In one aspect of the present disclosure, a method for extracting a region of interest is provided. The method may be implemented on at least one machine, and each of the at least one machine may have at least one processor and one storage. The method may include: acquiring image data in a first sectional plane, the image data in the first sectional plane including at least one first slice image and one second slice image; determining a first region of interest (ROI) in the first slice image; determining a second ROI in the second slice image; and determining, based on the first ROI, the second ROI, and characteristic information of the image data in the first sectional plane, a first volume of interest (VOI).

In some embodiments, the image data in the first sectional plane may include image data in a transverse plane, image data in a coronal plane, or image data in a sagittal plane.

In some embodiments, the method may further include: displaying the first ROI or the second ROI in a two-dimensional reconstruction view, and displaying the first VOI synchronously in a three-dimensional reconstruction view; and displaying the first ROI or the second ROI in the first VOI displayed in the three-dimensional reconstruction view.

In some embodiments, the determining a first VOI may include: determining, based on the characteristic information, whether the first ROI, the second ROI, or the first VOI satisfies a pre-determined condition; in response to a determination that the first ROI, the second ROI, or the first VOI does not satisfy the pre-determined condition: editing the first ROI or the second ROI; and generating, based on the edited first ROI or the edited second ROI, an edited first VOI.

In some embodiments, the method may further include: determining a first contour line of the first ROI, the first contour line including at least one first control point; determining a second contour line of the second ROI, the second contour line including at least one second control point; displaying the first contour line or the second contour line in the first VOI; and editing the at least one first control point of the first contour line or the at least one second control point of the second contour line in the first VOI to obtain an edited first ROI or an edited second ROI, and an edited first VOI.

In some embodiments, the pre-determined condition may relate to whether the first ROI, the second ROI, or the first VOI includes at least one of a blood vessel, calcified tissue, or fracture tissue.

In some embodiments, the method may further include: generating a first curve in the first slice image, wherein the first curve includes at least one first control point, and the first curve divides the first ROI into at least two regions; and generating a second curve in the second slice image, wherein the second curve includes at least one second control point, and the second curve divides the second ROI into at least two regions.

In some embodiments, the method may further include: generating, based on the at least one first control point of the first curve and the at least one second control point of the second curve, a first curved surface using an interpolation algorithm, the first curved surface dividing the first VOI into at least two portions.

In some embodiments, the method may further include: displaying the first curve or the second curve in a multiplanar reconstruction window; and synchronously displaying the first curved surface, the first curve, or the second curve in a volume rendering window.

In some embodiments, the method may further include: optimizing, based on the characteristic information of the image data, the first VOI to obtain a second VOI, the second VOI including at least one portion of the first VOI.

In some embodiments, the first VOI may include a third VOI, and the method may further include: performing, based on the first VOI, region growing of the third VOI at a first point in time; suspending region growing of the third VOI at a second point in time; determining, based on depth information of the image data and the first VOI, at least one portion of the third VOI, wherein the at least one portion of the third VOI includes at least one first voxel, and a depth relating to the first voxel is less than or equal to a depth relating to the image data; determining, based on the at least one portion of the third VOI, a first texture, the first texture including gray level distribution information of the at least one first voxel; and determining, based on the first texture and the first VOI, a second texture, the second texture including the first texture.

In some embodiments, the characteristic information may include gray level information.

In another aspect of the present disclosure, a method for extracting a region of interest is provided. The method may be implemented on at least one machine, and each of the at least one machine may have at least one processor and one storage. The method may include: acquiring image data in a first sectional plane, the image data in the first sectional plane including at least one first slice image and a second slice image; determining, based on the first slice image, a first set of control points, the first set of control points including at least two control points; determining, based on the second slice image, a second set of control points, the second set of control points including at least two control points; determining, based on the first set of control points, a first spline curve; determining, based on the second set of control points, a second spline curve; generating, based on the first spline curve and the second spline curve, a first curved surface; editing, based on the first curved surface, the first spline curve or the second spline curve; and generating, based on the edited first spline curve or the edited second spline curve, a second curved surface.

In some embodiments, the image data in the first sectional plane may include image data in a transverse plane, image data in a coronal plane, or image data in a sagittal plane.

In some embodiments, the editing the first spline curve or the second spline curve may include one or more of the following operations.

At least one control point of the first set of control points or at least one control point of the second set of control points may be adjusted based on the first curved surface. At least one control point of the first set of control points may be adjusted based on the first spline curve. At least one control point of the second set of control points may be adjusted based on the second spline curve.

In some embodiments, the editing the first spline curve or the second spline curve may include one or more of the following operations.

The first spline curve or the second spline curve may be edited based on characteristic information of the image data in the first sectional plane.

In some embodiments, the method may further include: displaying the first spline curve or the second spline curve in a multiplanar reconstruction window; and synchronously displaying the first curved surface, the first spline curve, or the second spline curve in a volume rendering window or a mesh rendering window.

In some embodiments, the method may further include: adjusting, based on the first curved surface, at least one control point of the first set of control points or at least one control point of the second set of control points in the volume rendering window or the mesh rendering window.

In another aspect of the present disclosure, a method for extracting a region of interest is provided. The method may be implemented on at least one machine, and each of the at least one machine may have at least one processor and one storage. The method may include: acquiring image data; generating, based on the image data, a first image using three-dimensional reconstruction, the first image including a first volume of interest (VOI), the first VOI including at least one first voxel; performing, based on the first image, region growing of the first VOI at a first point in time; suspending region growing of the first VOI at a second point in time; determining, based on depth information of the image data, a second VOI, wherein the second VOI includes at least one portion of the first VOI, the second VOI includes at least one second voxel, and a depth relating to the second voxel is less than or equal to a depth relating to the image data; generating, based on the second VOI, a first texture, the first texture including gray level distribution information of the at least one second voxel; and determining, based on the first texture and the first image, a second texture, the second texture including the first texture.

In some embodiments, the determining a second VOI may include: determining a first set of seed points, the first set of seed points including all the seed points growing from the first point in time to the second point in time; determining a second set of seed points, wherein the first set of seed points including the second set of seed points, and wherein a depth relating to the second set of seed points is less than or equal to the depth relating to the image data; determining, based on a plurality of three-dimensional coordinates of the second set of seed points, a plurality of two-dimensional projection coordinates of the second set of seed points; and determining, based on the plurality of two-dimensional projection coordinates of the second set of seed points, the second VOI.

In some embodiments, the determining a second VOI may further include: generating a third texture of the first VOI without considering the depth information of the image data, which includes: determining a third set of seed points at a third point in time, the third set of seed points including at least one portion of a plurality of seed points growing from the first point in time to the third point in time; determining, based on a plurality of three-dimensional coordinates of the third set of seed points, a plurality of two-dimensional projection coordinates of the third set of seed points; and determining, based on the plurality of two-dimensional projection coordinates of the third set of seed points, the third texture of the first VOI, the third texture including gray level distribution information of the at least one first voxel.

In some embodiments, the region growing of the first VOI may include: determining a number of extraction times of a plurality of seed points during the region growing from the first point in time to the fourth point in time; determining whether the number of extraction times of the plurality of seed points is less than or equal to a pre-determined value; in response to a determination that the number of extraction times of the plurality of seed points is less than or equal to the pre-determined value, decreasing a speed of generating a plurality of new seed points; and in response to a determination that the number of extraction times of the plurality of seed points is more than the pre-determined value, increasing the speed of generating the plurality of new seed points.

In another aspect of the present disclosure, a system for extracting a region of interest is provided. The system may include at least one processor, and a storage configured to store instructions. The instructions, when executed by the at least one processor, may cause the system to effectuate a method. The method may include: acquiring image data in a first sectional plane, the image data in the first sectional plane including at least one first slice image and one second slice image; determining a first region of interest (ROI) in the first slice image; determining a second ROI in the second slice image; and determining, based on the first ROI, the second ROI, and characteristic information of the image data in the first sectional plane, a first volume of interest (VOI).

In another aspect of the present disclosure, a non-transitory computer-readable medium is provided. The non-transitory computer-readable medium may include executable instructions. When executed by at least one processor, the executable instructions may cause the at least one processor to effectuate a method. The method may include: acquiring image data in a first sectional plane, the image data in the first sectional plane including at least one first slice image and one second slice image; determining a first region of interest (ROI) in the first slice image; determining a second ROI in the second slice image; and determining, based on the first ROI, the second ROI, and characteristic information of the image data in the first sectional plane, a first volume of interest (VOI).

In another aspect of the present disclosure, a system for extracting a region of interest is provided. The system may include at least one processor, and a storage configured to store instructions. The instructions, when executed by the at least one processor, may cause the system to effectuate a method. The method may include: acquiring image data in a first sectional plane, the image data in the first sectional plane including at least one first slice image and a second slice image; determining, based on the first slice image, a first set of control points, the first set of control points including at least two control points; determining, based on the second slice image, a second set of control points, the second set of control points including at least two control points; determining, based on the first set of control points, a first spline curve; determining, based on the second set of control points, a second spline curve; generating, based on the first spline curve and the second spline curve, a first curved surface; editing, based on the first curved surface, the first spline curve or the second spline curve; and generating, based on the edited first spline curve or the edited second spline curve, a second curved surface.

In another aspect of the present disclosure, a non-transitory computer-readable medium is provided. The non-transitory computer-readable medium may include executable instructions. When executed by at least one processor, the executable instructions may cause the at least one processor to effectuate a method. The method may include: acquiring image data in a first sectional plane, the image data in the first sectional plane including at least one first slice image and a second slice image; determining, based on the first slice image, a first set of control points, the first set of control points including at least two control points; determining, based on the second slice image, a second set of control points, the second set of control points including at least two control points; determining, based on the first set of control points, a first spline curve; determining, based on the second set of control points, a second spline curve; generating, based on the first spline curve and the second spline curve, a first curved surface; editing, based on the first curved surface, the first spline curve or the second spline curve; and generating, based on the edited first spline curve or the edited second spline curve, a second curved surface.

In another aspect of the present disclosure, a system for extracting a region of interest is provided. The system may include at least one processor, and a storage configured to store instructions. The instructions, when executed by the at least one processor, may cause the system to effectuate a method. The method may include: acquiring image data; generating, based on the image data, a first image using three-dimensional reconstruction, the first image including a first volume of interest (VOI), the first VOI including at least one first voxel; starting, based on the first image, region growing of the first VOI at a first point in time; suspending region growing of the first VOI at a second point in time; determining, based on depth information of the image data, a second VOI, wherein the second VOI includes at least one portion of the first VOI, the second VOI includes at least one second voxel, and a depth relating to the second voxel is less than or equal to a depth relating to the image data; drawing, based on the second VOI, a first texture, the first texture including gray level distribution information of the at least one second voxel; and determining, based on the first texture and the first image, a second texture, the second texture including the first texture.

In another aspect of the present disclosure, a non-transitory computer-readable medium is provided. The non-transitory computer-readable medium may include executable instructions. When executed by at least one processor, the executable instructions may cause the at least one processor to effectuate a method. The method may include: acquiring image data; generating, based on the image data, a first image using three-dimensional reconstruction, the first image including a first volume of interest (VOI), the first VOI including at least one first voxel; starting, based on the first image, region growing of the first VOI at a first point in time; suspending region growing of the first VOI at a second point in time; determining, based on depth information of the image data, a second VOI, wherein the second VOI includes at least one portion of the first VOI, the second VOI includes at least one second voxel, and a depth relating to the second voxel is less than or equal to a depth relating to the image data; drawing, based on the second VOI, a first texture, the first texture including gray level distribution information of the at least one second voxel; and determining, based on the first texture and the first image, a second texture, the second texture including the first texture.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The drawings described herein are used to provide further understanding of the present disclosure and serve as a part of the present disclosure. The exemplary embodiments and relevant descriptions are for the purpose of illustration, and not intended to limit the present disclosure. The same reference numerals represent the same structures throughout the drawings, and wherein.

DETAILED DESCRIPTION

Figure 1:
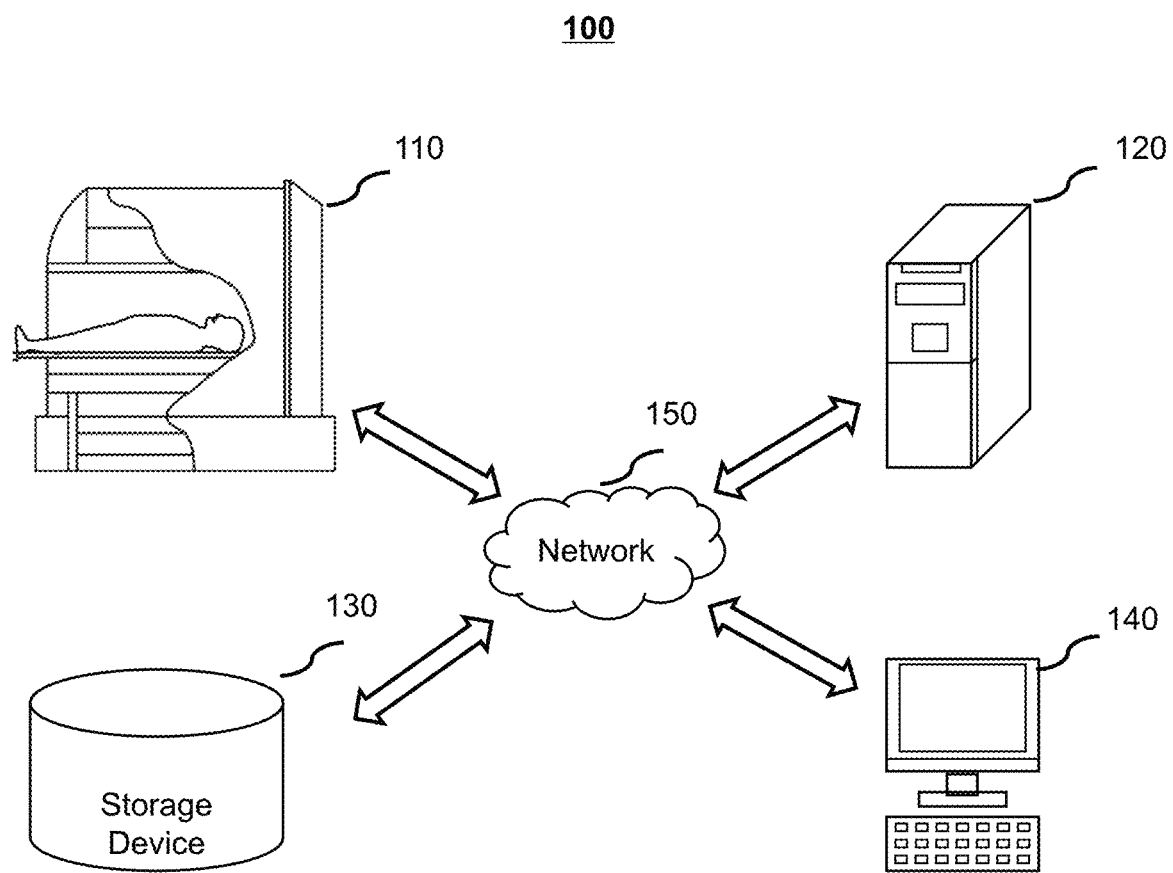
FIG. 1 is a schematic diagram illustrating an application scenario of an exemplary image processing system according to some embodiments of the present disclosure.

In the following detailed description, numerous specific details are set forth by way of examples in order to provide a thorough understanding of the relevant disclosure. Apparently, the drawings used in the following description only illustrate some examples or embodiments of the present disclosure. For those having ordinary skills in the art, the present disclosure may be applied to other similar circumstances according to the drawings without creative work. It should be appreciated that the exemplary embodiments are provided only to assist those skilled in the art to better understand and implement the present disclosure, not intended to limit the scope of the present disclosure in any means. The same numerals in the drawings represent the same structures or operations unless apparent from the language environment or otherwise clarified.

As used in the present disclosure and the claims, the singular forms "a," "an," "one" and "the" may be intended to include the plural forms as well, unless the context clearly indicates otherwise. Generally, the terms "comprises," "comprising," "includes," and/or "including" when used in the disclosure, specify the presence of stated steps and elements, but do not preclude the presence or addition of one or more other steps and elements.

Although the present disclosure makes various references to certain modules in the system according to some embodiments of the present disclosure, any number of different modules may be used and run on a client terminal and/or a server. The modules are illustrative only, and different aspects of the systems and methods may use different modules.

Flowcharts are used in the present disclosure to illustrate operations performed by the system according to some embodiments of the present disclosure. It should be understood that the preceding or following operations may not be necessarily performed exactly in order. Instead, various steps may be processed in reverse sequence and/or simultaneously. Moreover, other operations may also be added into these procedures, or one or more steps may be removed from these procedures.

In the process of image data processing, the extraction of a region of interest (ROI) or volume of interest (VOI) performed by the system may include information of image pixels or voxels that meet certain criteria extracted from a relatively large area. The system may extract the ROI or VOI based on corresponding characteristic information of pixels or voxels of an image. In some embodiments, the corresponding characteristic information of the pixels or voxels may include a texture structure, a gray level, an average gray level, a signal intensity, color saturation, contrast, luminance, or the like, or any combination thereof, associated with the image. In some embodiments, the spatial location characteristics of the pixels or voxels may be used for the extraction process of the ROI or VOI. It should be noted that the terms "tissue partition," "image segmentation," "image extraction" and "image classification" may represent the same operation.

It should be noted that the above descriptions of image data processing are only provided for the convenience of illustration, and not intended to limit the present disclosure to the scope of the mentioned embodiments. It should be understand that for those skilled in the art, after understanding the principles of the system and method, the modules may be combined in any means or connected to other modules as sub-systems. Various modifications and changes may be conducted on the form or details of the application fields of the system and method, without departing from the principles.

FIG. 1 is a schematic diagram illustrating an application scenario of an exemplary image processing system according to some embodiments of the present disclosure. The image processing system may include an imaging device 110, a data processing engine 120, a storage device 130, and an interactive device 140. The imaging device 110, the data processing engine 120, the storage device 130 and the interactive device 140 may communicate with each other via a network 150.

In some embodiments, the imaging device 110 may obtain data by scanning an object. The imaging device 110 may include but is not limited to computed tomography (CT), computed tomography angiography (CTA), positron emission tomography (PET), single photon emission computed tomography (SPECT), magnetic resonance imaging (MRI), digital subtraction angiography (DSA), ultrasound scanning (US), thermal texture maps (TTM), SPECT-MR, CT-PET, CE-SPECT, PET-MR, PET-US, SPECT-US, TMS-MR, US-CT, US-MR, X ray-CT, X ray-PET, or the like, or any combination thereof. In some embodiments, the object for scanning may be an organ, a body, a substance, an injured part, a tumor, or the like, or any combination thereof. In some embodiments, the object for scanning may be a head, a chest, an abdomen, an organ, skeletons, blood vessels, or the like, or any combination thereof. In some embodiments, the object for scanning may be vascular tissue of one or more body parts, a liver, etc. In some embodiments, the obtained data may be image data. The image data may be two-dimensional image data and/or three-dimensional image data. In a two-dimensional image, the smallest distinguishable element may be a pixel. In a three-dimensional image, the smallest distinguishable element may be a voxel. In a three-dimensional image, the image may include a series of two-dimensional slices or two-dimensional sections. A point (or element) of an image may be referred to as a voxel in a three-dimensional image and may be referred to as a pixel in a two-dimensional slice image where it is located. The terms "voxel" and/or "pixel" are only for the convenience of description, and not intended to limit the two-dimensional image and/or the three-dimensional image.

The format of the image data may include but is not limited to a Joint Photographic Experts Group (JPEG) format, a Tagged Image File Format (TIFF), a Graphics Interchange Format (GIF), a Kodak Flash Pix (FPX) format, a Digital Imaging and Communications in Medicine (DICOM) format, etc. In some embodiments, the imaging device 110 may transmit the obtained data via the network 150 to the data processing engine 120, the storage device 130 and/or the interactive device 140, etc. For instance, the image data may be transmitted to the data processing engine 120 for further processing, and may also be stored in the storage device 130.

The data processing engine 120 may process data. The data may include image data, data inputted by a user, etc. The image data may be two-dimensional image data and/or three-dimensional image data, etc. The data inputted by a user may include data processing parameters (e.g., the slice thickness, the slice gap, the number of slices, etc.), instructions associated with the system, etc. The data may be data obtained by the imaging device 110, data read from the storage device 130, data obtained from the interactive device 140, or data obtained from a cloud or an external device via the network 150. In some embodiments, the processing of the data may include data acquisition, classification, screening, transformation, computation, display, or the like, or any combination thereof. The data processing engine 120 may transmit the processed data to the storage device 130 for storage or to the interactive device 140. For example, the data processing engine 120 may process image data and transmit the processed image data to the interactive device 140 for display.

In some embodiments, the data processing engine 120 may include but is not limited to a Central Processing Unit (CPU), an Application Specific Integrated Circuit (ASIC), an Application Specific Instruction Set Processor (ASIP), a Physics Processing Unit (PPU), a Digital Processing Processor (DSP), a Field-Programmable Gate Array (FPGA), a Programmable Logic Device (PLD), a processor, a microprocessor, a controller, a microcontroller, or the like, or any combination thereof.

It should be noted that the data processing engine 120 illustrated above may be practically present in the system and may also implement corresponding functions via a cloud computing platform. The cloud computing platform may include but is not limited to a storage cloud platform mainly used for data storage, a computing cloud platform mainly used for data processing, a comprehensive cloud computing platform used for both data storage and data processing, etc. The cloud platform for use in the image processing system 100 may be a public cloud, a private cloud, a community cloud or a hybrid cloud, etc. For example, some medical images obtained by the image processing system 100 may be computed and/or stored via a cloud platform according to practical needs; some other medical images may be computed and/or stored by local processing modules and/or a storage within the system.

The storage device 130 may be set on a device with storage functions. The storage device 130 may store data collected from the imaging device 110 (e.g., data of an image taken by the imaging device 110) and various data generated in the work of the data processing engine 120. The storage device 130 may also store data inputted via the interactive device 140 (data inputted by a user). The storage device 130 may be local or remote. In some embodiments, the storage device 130 may be set on the data processing engine 120. The storage device 130 may include hierarchical database, network database, relational database, or the like, or any combination thereof. The storage device 130 may digitalize the information and store the information using an electrical, magnetic or optical storage device. The storage device 130 may be used for storing various information, such as programs, data, etc. The storage device 130 may be set on a device that stores information using electric energy, for example, a Random Access Memory (RAM), a Read Only Memory (ROM), etc. An RAM may include but is not limited to a decade counter tube, a selectron tube, a delay line memory, a Williams tube, a Dynamic Random Access Memory (DRAM), a Static Random Access Memory (SRAM), a thyristor RAM (T-RAM), and a zero-capacitor RAM (Z-RAM), etc. An ROM may include but is not limited to a magnetic bubble memory, a twister memory, a film storage, a magnetic plated wire memory, a magnetic core memory, a magnetic drum memory, an optical driver, a hard disk, a tape, an early Non-Volatile Random Access Memory (NVRAM), a phase change memory, a variable reluctance random access memory, a ferroelectric random access memory, a non-volatile SRAM, a flash memory, an electrically erasable programmable read only memory, an erasable programmable read only memory, a programmable read only memory, a mask read only memory, floating gate random access memory, nanometer random access memory, track memory, thyrecotor memory, programmable metallization cell, or the like, or any combination thereof. The storage device 130 may be set on a device using magnetic energy to store information, such as a hard disk, a soft disk, a tape, a magnetic core storage, a magnetic bubble storage, a USB drive, a flash memory, etc. The storage device 130 may be configured as an optical storage device, for example, a compact disk (CD), a digital video disk (DVD), etc. The storage device 130 may be configured as a magneto-optic storage device, such as a photomagnetic disk, etc. The method of information access in the storage device 130 may be random storage, serial access storage, read only memory, or the like, or any combination thereof. The storage device 130 may be set on a non-permanent memory or a permanent memory. The storage devices mentioned above are only exemplary, and not intended to limit the storage device used in the image processing system 100.

The interactive device 140 may receive, transmit and/or display data or information. In some embodiments, the interactive device 140 may have a part of or all of the functions of the data processing engine 120. For example, the interactive device 140 may perform further processing on the processing results of the data processing engine 120, such as displaying the data processed by the data processing engine 120. In some embodiments, the interactive device 140 and the data processing engine 120 may be a single integrated device. The integrated device may implement the functions of the data processing engine 120 as well as the interactive device 140. In some embodiments, the interactive device 140 may include but is not limited to an input device, an output device, or the like, or any combination thereof. The input device may include but is not limited to a device for inputting characters (e.g., a keyboard), an optical reading device (e.g., an optical mark reader, an optical character reader), a graphic input device (e.g., a mouse, an action bar, a light pen), an image input device (e.g., a camera, a scanner, a fax machine), an analog input device (e.g., a lingual analog digital conversion identification system), or the like, or any combination thereof. The output device may include but is not limited to a display device, a printing device, a plotting device, an image output system, a speech output system, a magnetic recording device, or the like, or any combination thereof. In some embodiments, the interactive device 140 may be a device having input functions as well as output functions, such as a desk-top computer, a lap-top computer, a smart phone, a tablet computer, a personal digital assistance (PDA), etc.

The network 150 may implement the intercommunication of the image processing system 100, receive information from the outside of the system, transmit information to the outside of the system, etc. In some embodiments, the imaging device 110, the data processing engine 120 and the interactive device 140 may be connected to each other by wired network, wireless network or a combination of both via network 150. The network 150 may be a single network or a combination of multiple types of network. In some embodiments, the network 150 may include but is not limited to a local area network, a wide area network, a public network, a private network, a wireless local area network, a virtual network, a metropolitan area network, a public telephone switched network, or the like, or any combination thereof. In some embodiments, the network 150 may include multiple types of network access points, such as wired or wireless network access points, base stations and/or internet exchange points through which data may be connected to the network 150 and information may be transmitted via the network 150.

It should be understand that the image processing system 100 illustrated in FIG. 1 may be implemented in various ways. For example, in some embodiments, the system 100 may be implemented by hardware, software or a combination of hardware and software. The hardware portion may be implemented by special logic circuit, and the software may be stored in a storage and executed by a suitable instruction execution system, such as a microcontroller or special hardware. Those skilled in the art may understand that the method and system above may be implemented by using computer executable instructions and/or may be implemented when embedded in the control code of a processor. For example, such code may be provided by a carrier medium such as a magnetic disk, a CD or a DVD-ROM, a programmable storage such as a read only memory (firmware) or a data carrier such as an optical medium or an electronic signal medium. The system and modules of the present disclosure may be implemented by, for example, very large scale integration circuit or gate array, semiconductors such as logic chips, transistors, etc., or the hardware circuit of a programmable hardware device such as field programmable gate array, a programmable logic device, etc. The system and modules of the present disclosure may also be implemented by, for example, software executed by different types of processors or a combination of the hardware circuit and software (e.g., firmware) mentioned above.

It should be noted that the above descriptions of the image processing system 100 are only for the convenience of illustration, and not intended to limit the present disclosure to the scope of the exemplary embodiments. It should be understand that for those skilled in the art, after understanding the principles of the system and method, the modules may be combined in any means or connected to other modules as sub-systems. Various modifications and changes may be conducted on the form or details of the application fields of the system and method, without departing from the principles. For instance, the storage device 130 may be configured on a cloud computing platform with the function of data storage, including but not limited to a public cloud, a private cloud, a community cloud or a hybrid cloud, etc. As another example, two or more of the imaging device 110, the data processing engine 120, the storage device 130 and the interactive device 140 may be directly configured in one device rather than communicating with each other via the network 150. Similar variations fall within the protection scope of the present disclosure.

Figure 2:
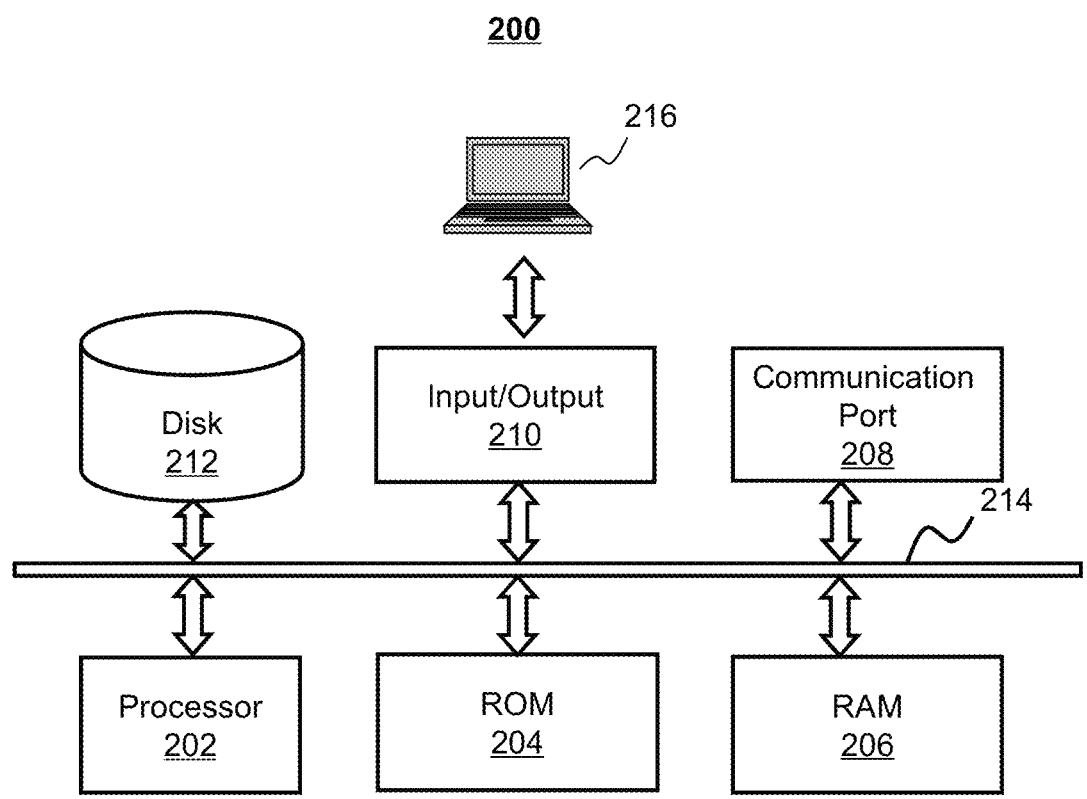
FIG. 2 is a schematic diagram illustrating the structure of an exemplary computing device according to some embodiments of the present disclosure.

FIG. 2 is a schematic diagram illustrating the structure of an exemplary computing device according to some embodiments of the present disclosure. As depicted, the computing device 200 may include a processor 202, a read only memory (ROM) 204, a random access memory (RAM) 206, a communication port 208, an input/output component 210, a disk 212, an inter communication bus 214 and a user interface 216. The communication bus 214 may implement the data communication between the components of the computing device 200. The processor 202 may execute program instructions to implement the functions of the one or more components, modules, units and subunits of the image processing system 100 described in the present disclosure. The processor 202 may include one or more processors. The communication port 208 may implement the data communication between the computing device 200 and other components of the image processing system 100 (e.g., the imaging device 110) via, for example, the network 150. The computing device 200 may also include different forms of program storage units and data storage units, such as the disk 212, the read only memory (ROM) 204 and the random access memory (RAM) 206, for storing various data documents processed by a computer or used for communication and possible program instructions executed by the processor 202. The input/output component 210 may implement the data input/output between the computing device 200 and other components (such as the user interface 216) and/or other components of the image processing system 100 (such as the storage device 130). The computing device 200 may transmit and receive information and data via the communication port 208 from the network 150.

Figure 3:
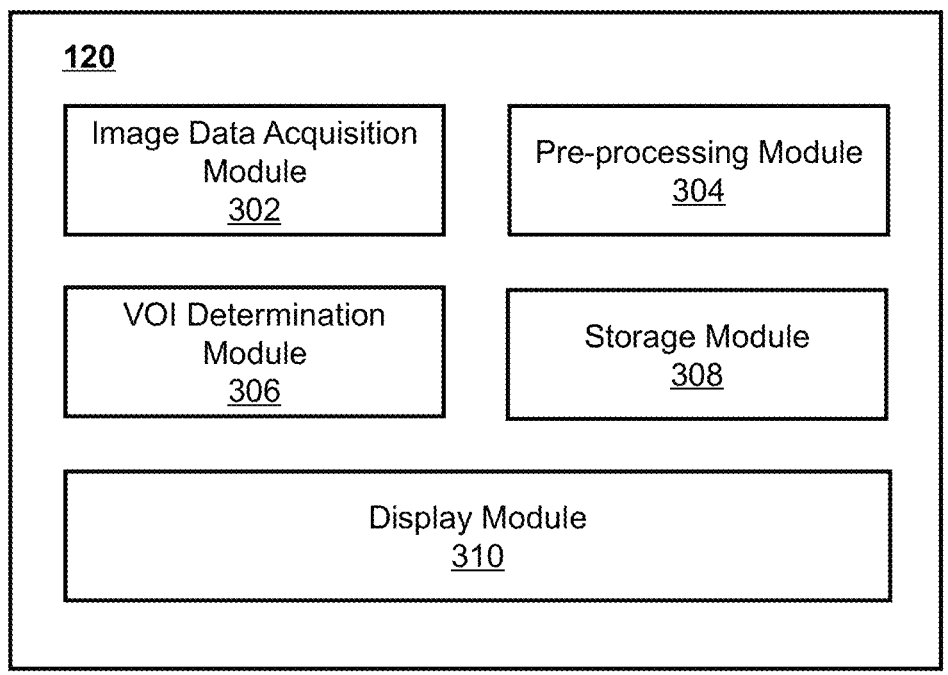
FIG. 3 is a schematic diagram illustrating an exemplary data processing engine according to some embodiments of the present disclosure.

FIG. 3 is a schematic diagram illustrating an exemplary data processing engine according to some embodiments of the present disclosure. The data processing engine 120 may include an image data acquisition module 302, a pre-processing module 304, a VOI determination module 306, a storage module 308 and a display module 310. In some embodiments, two or more of the image data acquisition module 302, the pre-processing module 304, the VOI determination module 306, the storage module 308 and the display module 310 may communicate with each other via the network 150. In some embodiments, two or more of the image data acquisition module 302, the pre-processing module 304, the VOI determination module 306, the storage module 308 and the display module 310 may communicate with each other via the communication bus 214.

The image data acquisition module 302 may obtain image data. The image may be a medical image. The medical image may include a CT image, a PET image, a SPECT image, an MRI image, an ultrasound image, or the like, or any combination thereof. The medical image may be a two-dimensional image and/or a three-dimensional image. In some embodiments, the image data acquisition module 302 may acquire image data from the imaging device 110, the storage device 130, the interactive device 140 and/or the storage module 308. In some embodiments, the acquisition of the image data may be real-time or non-real-time. In some embodiments, the acquired image data may be stored in the storage device 130, the storage module 308 or any other storage devices integrated in the system or separated from the system described in the present disclosure. In some embodiments, the acquired image data may be transmitted to other modules, units or subunits for further processing. For example, the image data acquisition module 302 may send the image data to the pre-processing module 304 to pre-process the image data. As another example, the image data acquisition module 302 may transmit the image data to the VOI determination module 306 for determining a VOI. For instance, the image data acquisition module may transmit the image data to the display module 310 for displaying the image.

The pre-processing module 304 may pre-process the image data. In some embodiments, the image data may include the image data acquired by the image data acquisition module 302. The image data may also include the intermediate image data generated during the work of the data processing engine 120 (e.g., the intermediate image data generated in the process of determining a VOI performed by the VOI determination module 306). The pre-processing may include initial positioning, image normalization, image reconstruction, image smoothing, image compression, image enhancement, image registration, image fusion, image geometric correction, image denoising, or the like, or any combination thereof. The pre-processing operation may be implemented by using a point operation, a geometric operation, etc. The point operation may include performing operations on pixels of the image data, including addition subtraction, multiplication and division, etc. The geometric operation may include performing operations on the image data, including transformation, zoom, rotation, distortion correction, etc. In some embodiments, pre-processed image data may be transmitted to other modules, units or sub-units for further processing. For example, the pre-processed image data may be transmitted to the VOI determination module 306 for determining the VOI. As another example, the pre-processed data may be transmitted to the storage module 309 for storage.

The VOI determination module 306 may determine one or more VOIs. In some embodiments, the VOI determination module 306 may process the image data and reconstruct a three-dimensional image to implement stereo displaying, editing and/or analyzing of a target of interest. A VOI may include one or more voxels of interest. In some embodiments, a VOI may include pixels in one or more slices of two-dimensional slice images. In some embodiments, the VOI may include at least a portion of the target of interest. In some embodiments, the target of interest may be a body, a substance, an injured part, a tumor, or the like, or any combination thereof. In some embodiments, the target of interest may be a head, a chest, an abdomen, a visceral organ, or the like, or any combination thereof. In some embodiments, the target of interest may be one or more specific organs or tissues, for example, a skeleton, a blood vessel, a trachea, a liver, or the like, or any combination thereof. In some embodiments, the VOI determination module 306 may determine one or more VOIs automatically, semi-automatically, or manually. For example, the VOI determination module 306 may automatically extract one or more VOIs based on one or more image segmentation algorithms. As another example, a user may determine one or more VOIs manually by the interactive device 140. As another example, a user may manually modify or change the generated VOI, or perform other manual operations on the generated VOI.

In some embodiments, the automatic determination of the VOI(s) may be performed based on one or more three-dimensional reconstruction techniques. The three-dimensional reconstruction techniques may include a surface rendering algorithm, a volume rendering algorithm, and a mesh rendering algorithm, etc. The surface rendering algorithm may a surface of a VOI. The surface rendering algorithm may segment the surface of the VOI to be determined in two-dimensional slice image(s), and then form the surface of the VOI by geometric element interpolation, and render and/or blank the surface of the VOI according to an illumination model, a dark model, etc. An image obtained through the surface rendering algorithm may be displayed on the display module 310 so that a user may easily check the results of surface rendering. The surface rendering algorithm may include a boundary contour line representation, a surface rendering algorithm based on voxels, a surface representation, etc. The boundary contour line representation (e.g., the triangular fitting surface algorithm) may extract the contour lines in the slice image(s) based on one or more image segmentation algorithms, and then stack the contour lines corresponding to one or more two-dimensional slice images to represent the surface boundary of the VOI. The surface rendering algorithm based on voxels may generate the surface of the VOI in voxel level. First of all, the VOI determination module 306 may extract the object of interest from a background using a threshold segmentation method, and then determine the voxels constituting the surface of the VOI by deep traversal searching. For example, the voxels located on the proximal surface of the VOI and the background may constitute the surface of the VOI. The surface representation may reconstruct the surface based on the boundary contour lines of the VOI. For instance, the VOI determination module 306 may segment the surface of the VOI into different regions based on a plurality of boundary contour lines, and fill the regions among the adjacent boundary contour lines using small planes (or curved surfaces) of triangles or polygons based on one or more plane filling algorithms (e.g., a seed filling algorithm, an injection filling algorithm, a boundary filling algorithm, etc.) so that the surface of the VOI may be formed. The surface representation may include a cuberille algorithm, a marching cubes algorithm, and a dividing cubes algorithm, etc.

As for volume rendering, the VOI determination module 306 may consider each pixel in a two-dimensional slice image as a hexahedral element (i.e., a voxel) in a three-dimensional space, cause a virtual light ray to pass through a plurality of two-dimensional slice images and analyze the transmission, scattering and reflection effects of each voxel where the virtual light ray passes. As a result, comprehensive characteristic information of a plurality of voxels where the virtual light ray passes may be obtained. The volume rendering algorithm may include a spatial domain algorithm, a transformation domain algorithm, etc. The spatial domain algorithm may directly process and display the image data, such as a ray tracing algorithm, a splatting algorithm, a shear-deformation algorithm, etc. The transformation domain algorithm may transform the image data to a transformation domain and then process and display the image. Exemplary transformation domain algorithms may include frequency domain volume rendering, volume rendering based on wavelet, etc. The image data may be the image data acquired by the image data acquisition module 302 or the image data pre-processed by the pre-processing module 304.

In some embodiments, the determination of the VOI may further be performed based on three-dimensional surface model reconstruction techniques, such as a multiplanar reconstruction (MPR), a maximum intensity projection (MIP), a surface shaded display (SSD), or the like, or any combination thereof. In some embodiments, the image data processed by the VOI determination module 306 may be transmitted to other modules, units or sub-units for further processing. For instance, the image data processed by the VOI determination module 306 may be transmitted to the display module 310 for display. In some embodiments, the VOI determination module 306 may determine the pixels/voxels corresponding to a VOI based on one or more image segmentation algorithms, and then determine the VOI using one or more three-dimensional reconstruction techniques. The image segmentation algorithm may be any one of the image segmentation algorithms described in the present disclosure (e.g., a region growing).

The storage module 308 may store data from the image data acquisition module 302, the pre-processing module 304, the VOI determination module 306 and/or the display module 310. The storage module 308 may include storage devices in the system (e.g., the storage device 130, the disk 212, the ROM 204, the RAM 206, etc.) and/or storage devices external to the system. The storage module 308 may be practically present in the system or implement the functions of data storage and data access via a cloud computing platform.

The display module 310 may display image data. In some embodiments, the image data may include the image data acquired by the image data acquisition module 302 and/or the intermediate image data generated during the work of the data processing engine 120. The intermediate image data may be the image data pre-processed by the pre-processing module 304, the intermediate data generated during the process of determining a VOI by the VOI determination module 306 (e.g., two-dimensional slice images of an ROI) or the VOI determined by the VOI determination module 306. In some embodiments, the display module 310 may include a display window for two-dimensional images, a display window for three-dimensional images, etc. to display the image data in two dimensions or three dimensions. In some embodiments, the display module 310 may display two-dimensional image information in the display window for three-dimensional images. For instance, during the process of determining the VOI, the display module 310 may display the determined VOI in the display window for three-dimensional images or making mark(s) on the VOI and display one or more corresponding ROIs. In some embodiments, the display module 310 may respond to information from the interactive device 140 and adjust the displayed image regions, the angles of view for display, display effects, etc. For example, a user may drag, rotate or switch the display window of an image using the interactive device 140 (e.g., a mouse) and observe a VOI from different views. As another example, a user may select a certain ROI (or VOI) using the interactive device 140 (e.g., a mouse) and then zoom in or out for display, etc. As a further example, a user may change a slice thickness of one or more two-dimensional slice images, and the display module 310 may re-display the image data according to the information of the adjusted slice thickness.

It should be noted that the above descriptions of the data processing engine 120 are only for the convenience of illustration, and not intended to limit the present disclosure to the scope of the exemplary embodiments. It should be understand that for those skilled in the art, after understanding the principles of the system and method, the modules may be combined in any means or connected to other modules as sub-systems. Various modifications and changes may be conducted on the form or details of the application fields of the system and method, without departing from the principles. In some embodiments, the image data acquisition module 302, the pre-processing module 304, the VOI determination module 306, the storage module 308 and the display module 310 may be different modules implemented on one device or system. In some embodiments, a multi-functional module may implement the functions of two or more modules described above. For example, the image data acquisition module 302 and the pre-processing module 304 may be two separate modules or integrated into one module, wherein the integrated module may have the function of image data acquisition as well as the function of pre-processing. As another example, the VOI determination module 306 and the pre-processing module 304 may be two separate modules or integrated into one module, wherein the integrated module may have the function of pre-processing as well as the function of determining the VOI. In some embodiments, the display module 310 may be integrated into the interactive device 140. In some embodiments, various modules may share one storage module or have their own storage modules, etc. Similar variations fall within the protection scope of the present disclosure.

Figure 4:
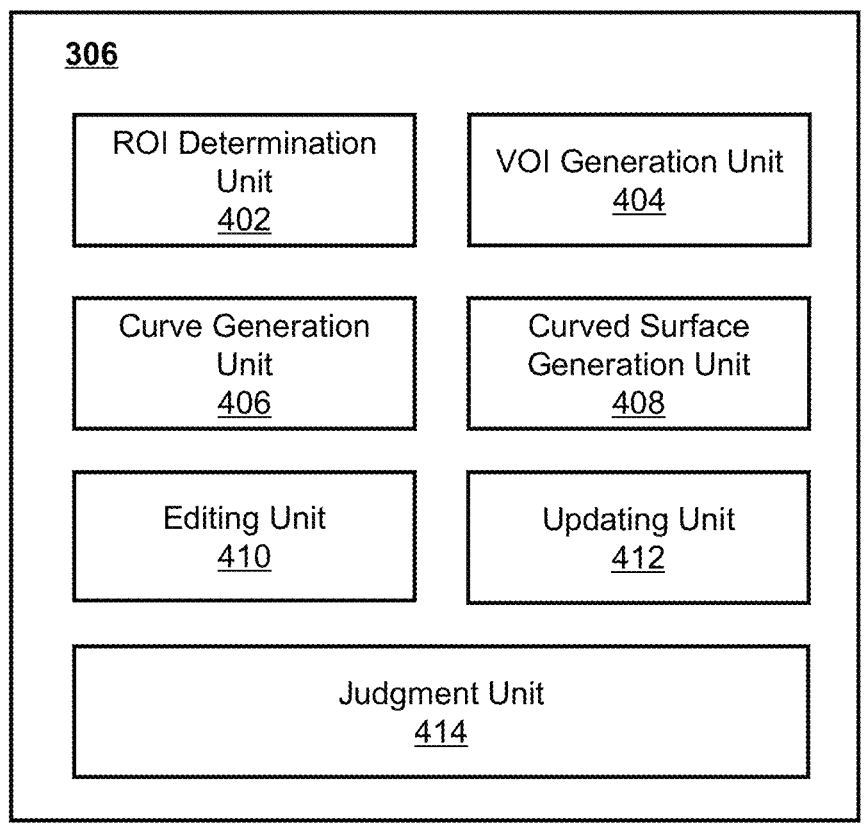
FIG. 4 is a schematic diagram illustrating an exemplary VOI determination module according to some embodiments of the present disclosure.

FIG. 4 is a schematic diagram illustrating an exemplary VOI determination module according to some embodiments of the present disclosure. The VOI determination module may include an ROI determination module 402, a VOI generation module 404, a curve generation unit 406, a curved surface generation unit 408, an editing unit 410, an updating unit 412, and a judgment unit 414. In some embodiments, the ROI determination unit 402, the VOI generation unit 404, the curve generation unit 406, the curved surface generation unit 408, the editing unit 410, the updating unit 412 and the judgment unit 414 may communicate with two or more described units or other devices or modules of the image processing system 100 (e.g., the storage device 130) via the network 150. In some embodiments, the ROI determination unit 402, the VOI generation unit 404, the curve generation unit 406, the curved surface generation unit 408, the editing unit 410, the updating unit 412 and the judgment unit 414 may implement the communication with two or more described units or the communication with other devices or modules of the image processing system 100 (e.g., the storage device 130) via the communication bus 214.

The ROI determination unit 402 may determine one or more ROIs. An ROI may include one or more pixels with characteristic information. The characteristic information may include a texture structure, a gray level, an average grey level, a signal intensity, color saturation, contrast, luminance, or the like, or any combination thereof. The ROI may include an ROI counter line and/or pixels within the contour line. The ROI contour line may be an approximately successive curve including a plurality of scattered pixels. The ROI contour line may be a closed or non-closed curve. In some embodiments, the ROI may include pixels corresponding to an organ (e.g., a blood vessel, a liver, etc.), normal tissue, a tumor, a nodule, injured tissue, calcified tissue, or the like, or any combination thereof. In some embodiments, the ROI determination unit 402 may determine one or more ROI contour lines, the characteristic information of the ROI, etc., in one or more two-dimensional slice images. In some embodiments, the determined ROI may be transmitted to other modules, units or sub-units for further processing. For example, the ROI determination unit 402 may transmit the determined ROI to the VOI generation unit 404 for generating a VOI. As another example, the ROI determination unit 402 may transmit the determined ROI to the editing unit 410 for editing the ROI.

The VOI generation unit 404 may generate one or more VOIs. In some embodiments, the VOI may include one or more voxels with characteristic information. The characteristic information may include a texture structure, a gray level, an average gray level, a signal intensity, color saturation, contrast, luminance, or the like, or any combination thereof. The VOI may include voxels corresponding to an organ (e.g., a blood vessel, a liver, etc.), normal tissue, a tumor, a nodule, injured tissue or calcified tissue, or the like, or any combination thereof. The VOI may include a contour surface and/or voxels within the contour surface. The VOI contour surface may be an approximately successive curved surface including a plurality of scattered voxels. The VOI contour surface may be a closed or a non-closed curved surface. In some embodiments, the VOI generation unit 404 may determine the VOI contour surface, the characteristic information of the voxels of the VOI, etc. The characteristic information of the voxels of the VOI may be determined based on the characteristic information of pixels in one or more slice images. For example, an interpolation algorithm may be performed on the pixels in multiple slice images to obtain voxels and corresponding characteristic information.

In some embodiments, the VOI generation unit 404 may generate one or more VOIs automatically, semi-automatically or via a manual input of a user. For example, the VOI generation unit 404 may extract one or more VOIs automatically based on one or more image segmentation algorithms. As another example, a user may manually sketch the contour lines of the VOI via the interactive device 140. As a different example, a user may manually sketch the contour lines of one or more ROIs via the interactive device 140 so that the VOI generation unit 404 may generate the VOI based on the contour lines of the ROI. As another example, a user may manually modify or change the generated VOI. In some embodiments, the VOI generation unit 404 may generate a VOI based on at least two counter lines of the ROI. In some embodiments, the generated VOI may be transmitted to other modules, units or sub-units for further processing. For example, the VOI generation unit 404 may transmit the generated VOI to the judgment unit 414 for determining whether the VOI satisfies a pre-determined condition. As another example, the VOI generation unit 404 may transmit the generated VOI to the editing unit 410 for editing or optimizing the VOI.

The curve generation unit 406 may generate one or more spline curves. A spline curve may include one or more control points. The control points may refer to points for determining a general shape and a general trend of the spline curve. A control point may be a pixel in a two-dimensional slice image or a pixel in an image generated after an interpolation conducted on the pixels in one or more two-dimensional slice images. The spline curve may be a curve obtained according to the interpolation fitting of a plurality of control points. The spline curve may be a continuous curve. In some embodiments, one or more control points of a spline curve may be located in different two-dimensional images. The spline curve may be a two-dimensional curve in a certain plane of a three-dimensional image (e.g., a traverse plane, a coronal plane, a sagittal plane or a plane with any inclination angle in the three-dimensional space), or a three-dimensional curve that spans a plurality of planes. In some embodiments, the spline curve may be a closed curve. For instance, two endpoints of the spline curve may coincide each other or the distance between the two endpoints is within a pre-determined threshold scope. In some embodiments, the spline curve may be a non-closed curve. For instance, the distance between two endpoints of the spline curve is beyond a pre-determined threshold.

In some embodiments, the curve generation unit 406 may generate a closed spline, for example, a counter line of an ROI. In some embodiments, the curve generation unit 406 may generate a non-closed spline, for instance, a segmentation line that segments one ROI into at least two portions. In some embodiments, the spline curve may be drawn manually. For example, a user may manually draw a counter line of an ROI or a segmentation line of an ROI via the interactive device 140. As another example, a user may determine one or more control points in an image via the interactive device 140, and then the curve generation unit 406 may generate a corresponding spline curve based on the control points. In some embodiments, the spline curve may be drawn automatically. For instance, the curve generation unit 406 may automatically detect a contour (or boundary) of an ROI or a segmentation line of different regions within an ROI based on characteristic information of ROI pixels extracted by the ROI determination unit 402. In some embodiments, the curve generation unit 406 may determine one or more control points based on characteristic information of an image, and then generate a spline curve based on the control points. In some embodiments, the generated spline curve may be further processed by the ROI determination unit 402. For instance, the ROI determination unit 402 may extract characteristic information of an ROI based on the spline curve generated by the curve generation unit 406.

The curved surface generation unit 408 may generate one or more curved surfaces. A curved surface may be displayed in the form of a mesh or a polygon mesh including one or more elements, for example, one or more vertices, one or more edges, one or more faces defining the shape of a polyhedral object, etc. The curved surface may be a flat face (e.g., all the elements in the curved surface may be in the same plane) or a curved face. The curved surface may include a closed curved surface or a non-closed curved surface. The closed curved surface may be a face (or a contour surface) of a VOI. The non-closed curved surface may be a segmentation face that segments one VOI into at least two portions. In some embodiments, the curved surface generation unit 408 may generate a curved surface based on one or more spline curves. For instance, the curved surface generation unit 408 may generate a mask based on one or more spline curves, and then transform the mask into a mesh. Specifically, a mesh may be generated based on the one or more spline curves by an interpolation among the curves, wherein the mesh may be a mask image, i.e., the gray level of pixels or voxels in the mesh is 1 and the gray level of pixels or voxels outside the mesh is 0. The curved surface generation unit 408 may further segment the mask into normative mesh structures, wherein the mesh structures may include a plurality of mesh points. Then, the curved surface generation unit 408 may determine whether the mesh points are within a pre-determined scope of control points on the one or more spline curves. If the mesh points are within the pre-determined scope, then the mesh points may belong to the mesh; if the mesh points are beyond the pre-determined scope, then the mesh points may not belong to the mesh. In some embodiments, the curved surface generation unit 408 may further adjust the location(s) of the mesh point(s) to locate the mesh points in the pre-determined scope.

In some embodiments, the curved surface generation unit 408 may generate a closed curve surface, for example, a contour surface of a VOI. In some embodiments, the curved surface generation unit 408 may generate a non-closed curved surface, for example, a segmentation face of different regions in a VOI. In some embodiments, the non-closed curved surface may segment the target of interest into at least two portions. For instance, a user may need to segment a VOI (e.g., a liver) based on functions of the VOI, wherein the user may sketch a spline curve in each slice of two-dimensional slice images (e.g., two-dimensional images in a traverse plane, a sagittal plane or a coronal plane) of a liver, and the spline curve may segment the liver region into at least two portions in the current slice image, and then the curved surface generation unit 408 may generate a mesh based on a plurality of sketched spline curves. In a three-dimensional image, the curved surface may segment a liver into at least two portions. In some embodiments, the generated mesh may be further processed by the VOI generation unit 404. For instance, the VOI generation unit 404 may extract characteristic information of a VOI based on the mesh generated by the curved surface generation unit 408.

The editing unit 410 may edit intermediate image data generated during the working process of the VOI determination module 306. The intermediate image data may include an ROI determined by the ROI determination unit 402, a spline curve generated by the curve generation unit 406, a VOI generated by the VOI generation unit 404 and/or a mesh generated by the curved surface generation unit 408, etc. The process of the editing may be implemented manually or automatically. For example, a user may adjust the contour line of an ROI via the interactive device 140 (e.g., a mouse). As another example, the editing unit 410 may automatically adjust or optimize an ROI contour line based on characteristic information of an image. The process of the editing may be performed based on a two-dimensional view (or a two-dimensional image) or a three-dimensional view (or a three-dimensional image). For example, determined ROI contour line(s) may be edited in a two-dimensional view. As another example, the ROI contour line(s) of a VOI or the contour surface of a VOI may be edited in a three-dimensional view. In some embodiments, the edited ROI or VOI may be further processed by other modules, units or sub-units. For example, the editing unit 410 may provide the edited ROI or VOI to the updating unit 412 for updating the determined ROI or the generated VOI. As another example, the editing unit 410 may provide the edited ROI or VOI to the judgment unit 414 for determining whether to continue editing the edited ROI or VOI.

The updating unit 412 may update intermediate image data generated during the working process of the VOI determination module 406. In some embodiments, the intermediate image data may be an ROI determined by an ROI determination unit 402, a spline curve generated by the curve generation unit 406, a VOI generated by the VOI generation unit 404 and/or a curved surface generated by the curved surface generation unit 408, etc. In some embodiments, after edited by the editing unit 410, the ROI determined by the ROI determination unit 402 or the VOI generated by the VOI generation unit 404 may be used by the updating unit 412 for generating a new ROI or VOI. In some embodiments, after edited by the editing unit 410, the curve generated by the curve generation unit 406 or the curved surface generated by the curved surface generation unit 408 may be used by the updating unit 412 for generating a new curve or curved surface. In some embodiments, the updating unit 412 may provide the updated curve or curved surface to the ROI determination unit 402 for re-determining an ROI or to the VOI generation unit 404 for re-generating a VOI.

The judgment unit 414 may conduct a judgment on intermediate image data generated during the working process of the VOI determination module 306. In some embodiments, the intermediate image data may include an ROI determined by the ROI determination unit 402, a spline curve generated by the curve generation unit 406, a VOI generated by the VOI generation unit 404 and/or a curved surface generated by the curved surface generation unit 408, etc. For instance, the judgment unit 414 may conduct a judgment on whether the ROI determined by the ROI determination unit 402 (or the VOI generated by the VOI generation unit 404) satisfies a pre-determined condition or user requirement(s). The pre-determined condition may be pre-determined by the system or a user. The pre-determined condition may relate to whether the ROI or VOI includes an organ (e.g., a blood vessel), a tumor, injured tissue, etc. The user requirement(s) may include whether the ROI (or VOI) is considered as suitable by a user, whether the ROI (or VOI) needs to be edited, adjusted or optimized, etc. In some embodiments, the judgment unit 414 may provide the judging results to other modules, units or sub-units for further processing. For instance, if the judgment unit 414 determines that the curved surface generated by the curved surface generation unit 408 does not satisfy the user requirement(s), then the system may automatically adjust (or a user may manually adjust) the spline curve, and the curved surface generation unit 408 may re-generate a curved surface based on the adjusted spline curve.

In some embodiments, the ROI determined by the ROI determination unit 402, the VOI generated by the VOI generation unit 404, the curve generated by the curve generation unit 406 and/or the curved surface generated by the curved surface generation unit 408, the real-time editing results or relevant intermediate image data of the editing unit 410 may be displayed by the display module 310. For example, when a user is sketching a contour line of an ROI in a two-dimensional slice image in a display window for two-dimensional images (e.g., a traverse multiplanar reconstruction window), the display module 310 may conduct spatial orientation on the ROI and display other sectional planes (e.g., a coronal plane, a sagittal plane) in the display window for two-dimensional images, or display marks of the ROI at a corresponding location of the ROI in the image in the display window for three-dimensional images (e.g., a volume rendering window). As another example, when a user is sketching a contour line of an ROI in each slice image of a plurality of two-dimensional slice images, the VOI generation unit 404 may generate a VOI based on at least two sketched ROIs. Furthermore, the display module 310 may display the generated VOI in the display window for three-dimensional images in real-time.

It should be noted that the above descriptions of the VOI determination module 306 are only for the convenience of illustration, and not intended to limit the present disclosure to the scope of the exemplary embodiments. It should be understand that for those skilled in the art, after understanding the principles of the system and method, the modules may be combined in any means or connected to other modules as sub-systems. Various modifications and changes may be conducted on the form or details of the application fields of the system and method, without departing from the principles. In some embodiments, two or more of the ROI determination module 402, the curve generation unit 406, the VOI generation module 404, the curved surface generation unit 408, the editing unit 410, the updating unit 412 and the judgment unit 414 may be different units implemented in one device or module, or may be integrated into one unit that may implement the functions of the two or more units. For instance, the editing unit 410 and the updating unit 412 may be two separate units, or may be integrated into one unit having an editing function as well as an updating function. As another example, the ROI determination unit 402 and the VOI generation unit 404 may share one editing unit 410, updating unit 412 or judgment unit 414, or may have respective editing units, updating units or judgment units. As a further example, the ROI determination unit 402 and the curve generation unit 406 may be integrated into a single unit, while the VOI generation unit 404 and the curved surface generation unit 408 may be integrated into a single unit. Similar variations fall within the protection scope of the present disclosure.

Figure 5:
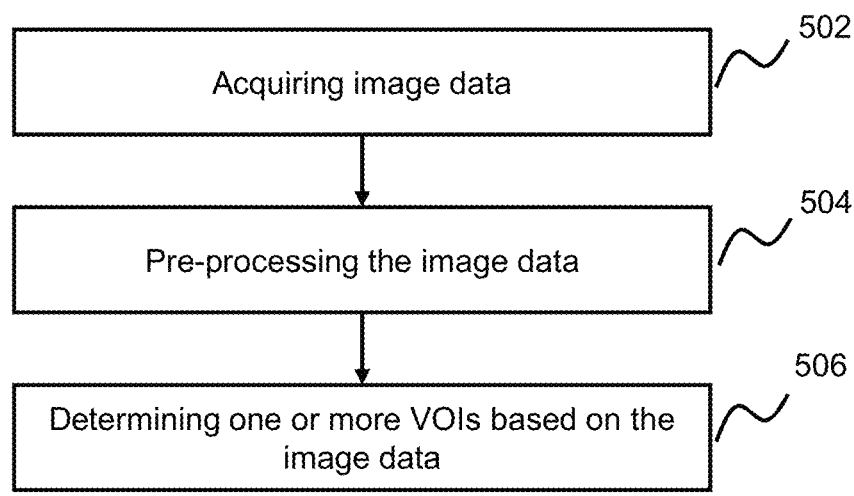
FIG. 5 is a flowchart of an exemplary process for image processing according to some embodiments of the present disclosure.

FIG. 5 is a flowchart of an exemplary process for image processing according to some embodiments of the present disclosure. The image processing process 500 may include acquiring image data in 502, pre-processing the image data in 504 and determining VOI(s) based on the image data in 506. In some embodiments, the determining VOI(s) based on the image data in 506 may further refer to descriptions of FIG. 6 in the present disclosure.

In 502, image data may be acquired. In some embodiments, the operation of acquiring image data may be performed by the image data acquisition module 302. In some embodiments, the image data may be one or more two-dimensional slice images acquired by scanning an object. The scanned object may be an organ, a body, a substance, an injured part, a tumor, or the like, or any combination thereof. In some embodiments, the scanned object may be a head, a chest, an abdomen, an organ (such as a skeleton, a blood vessel, etc.), or the like, or any combination thereof. In some embodiments, the image data may be two-dimensional slice image sequence(s) within a reconstruction scope obtained from the two-dimensional slice image(s), or two-dimensional slice image sequence(s) corresponding to a target of interest. The scanned object may include the target of interest. The target of interest may be a portion of the scanned object. For example, when performing liver segmentation, the image data may be a plurality of two-dimensional slice images acquired by scanning a chest and/or an abdomen, and the target of interest may be the liver. As another example, the image data may be two-dimensional slice image sequence(s) corresponding to a liver, and the target of interest may be abnormal tissue in the liver (e.g., a tumor, etc.).

In some embodiments, the image data may be the image data of other sectional planes (e.g., sagittal plane, coronal plane) obtained by performing a three-dimensional reconstruction technique based on one or more two-dimensional slice images acquired by scanning a target. The three-dimensional reconstruction technique may be multiplanar reconstruction (MPR). The MPR may stack a plurality of axial images (e.g., traverse images) within the scanning scope, and then perform image reformation on a specified tissue or in a specified scope in the coronal plane, the sagittal plane or an oblique plane with any angle, so that a new slice image in coronal plane, sagittal plane or oblique plane with any angle may be generated.

In 504, the image data acquired in 502 may be pre-processed. In some embodiments, the operation of pre-processing may be performed by the pre-processing module 304. In some embodiments, the pre-processing may include preliminary orientation, enhancement, interpolation processing, morphological processing, noise removal, or the like, or any combination thereof. The preliminary orientation may determine a general region where an ROI is located based on the image data, and thus the subsequent process of determining the ROI may be simplified. The preliminary orientation may be performed automatically, semi-automatically or manually. The enhancement processing may highlight one or more structures or regions in the image. The enhancement processing may include a spatial domain enhancement (e.g., local mean algorithm, median filter algorithm, etc.), a frequency domain enhancement (e.g., low-pass filtering, high-pass filtering, etc.).

The interpolation processing may uniform the sizes of pixels or voxels in the image. In some embodiments, the interpolation processing may be performed on a single two-dimensional slice image so that the pixels in the image may have a uniform size. The interpolation processing for a single slice image may include a nearest neighbor interpolation, a natural neighbor interpolation, a bilinear interpolation, a cubic interpolation, or the like, or any combination thereof. In some embodiments, the interpolation processing may be performed between a plurality of two-dimensional slice images to acquire cubic voxels with a uniform size. The interpolation processing between slice images may include an interpolation based on image gray levels, a shape-based target interpolation, an image interpolation based on matching, or the like, or a combination thereof. The interpolation based on image gray levels may include nearest neighbor interpolation, linear interpolation, spline interpolation, etc. The shape-based target interpolation may include segmenting two-dimensional images, extracting ROIs and then performing an interpolation so that an intermediate object contour with continuous variations may be generated. The image interpolation based on matching may perform image interpolation based on the matching of characteristic information such as boundary contour information, structural information of an object, gray level information, structure trend information, etc.

The morphology processing may process the shapes in image data for the purpose of analyzing and recognizing a target by using elements having morphological structures (e.g., structural element with 3×3, 5×8, or any other size or shape). Morphology processing algorithms may include a dilation operation, an erosion operation, an opening operation, a close operation, or the like, or any combination thereof. The noise removal may remove interference in image data or an ROI caused by machine noise, target movement, etc. Denoising algorithms may include neighborhood averaging, median filtering, low-pass filtering, Fourier transformation, wavelet transformation, total variation denoising, or the like, or any combination thereof.

In 506, one or more VOIs may be determined based on the image data. In some embodiments, the operation of determining the VOI(s) may be performed by the VOI determination module 306. In some embodiments, the image data may be the image data acquired in 502 or the image data pre-processed in 504.

In some embodiments, the determination of the VOI may include processing the image data, reconstruct a three-dimensional image to implement stereo display, editing or analysis, or the like, of the target of interest. In some embodiments, the determination of the VOI may include the generation of VOI contour surface (or VOI curved surface). The generation of VOI contour surface may be generated using one or more curved surface reconstruction algorithms based on boundary contour lines. The curved surface reconstruction algorithms based on boundary contour lines may include a triangular surface reconstruction algorithm, a curved surface reconstruction algorithm for volume data, etc. The triangular surface reconstruction algorithm may include determining an ROI contour line in a two-dimensional image, and then determine a corresponding contour line and special points (e.g., a cusp or a turning point where changes occur to the concave-convex degree of the curved surface) in an adjacent slice image, and the triangular surface may be rendered based on points of boundary of the adjacent slice image, wherein the special points may be regarded as the points of boundary of the adjacent slice image. The triangular surface reconstruction algorithm may include a contour connection algorithm, an opaque cubes algorithm, a marching cubes algorithm, a dividing cubes algorithm, etc. The curved surface reconstruction algorithm for volume data may construct an entity structure of the VOI using spatial units (e.g., a unit including one or more voxels), and reconstruct the VOI contour surface by extracting non-shared faces of the spatial units. The curved surface reconstruction algorithm for volume data may include Delaunay tetrahedron reconstruction, a parallel hexahedron reconstruction, a marching tetrahedron reconstruction, etc.

In some embodiments, the image processing process 500 may further include displaying the VOI in a two-dimensional view and/or a three-dimensional view. In some embodiments, the image processing process 500 may further include determining characteristic information of VOI voxels (e.g., gray level values, color, luminance, or other information of the voxels). For instance, the surface of the VOI contour surface and the gray level values of voxels in the contour surface may be extracted based on the determined VOI contour surface. In some embodiments, the characteristic information of VOI voxels may be determined based on interpolation between two-dimensional slice images. In some embodiments, the image processing process 500 may further include optimizing the VOI based on the characteristic information of VOI voxels. For example, during a process of segmenting a tumor, the VOI may include the tumor, and the image processing process 500 may remove blood vessels, injured tissue, calcified tissue or other tissue located on the surface of the tumor based on the gray level information of voxels in the extracted VOI.

It should be noted that the above descriptions of the image processing process 500 are only for the convenience of illustration, and not intended to limit the present disclosure to the scope of the exemplary embodiments. It should be understand that for those skilled in the art, after understanding the principles of the system and method, the modules may be combined in any means or connected to other modules as sub-systems. Various modifications and changes may be conducted on the form or details of the application fields of the system and method, without departing from the principles. For instance, operation 504 may be omitted from the image processing process 500. Similar variations fall within the protection scope of the present disclosure.

Figure 6A:
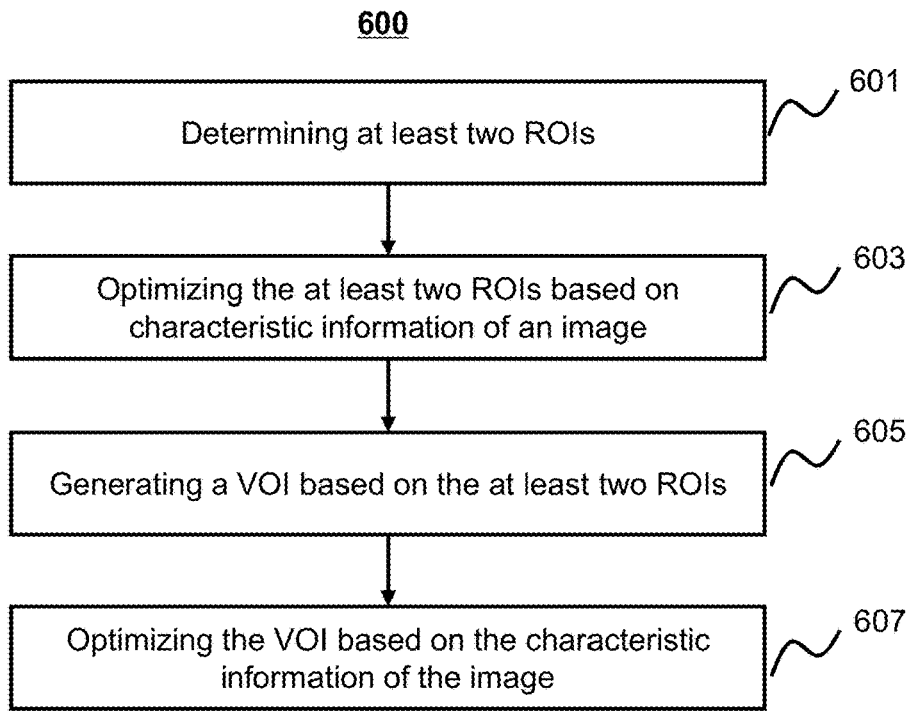
FIG. 6A is a flowchart of an exemplary process for determining a VOI according to some embodiments of the present disclosure.

FIG. 6A is a flowchart of an exemplary process for determining a VOI according to some embodiments of the present disclosure. In some embodiments, the operation 506 of determining VOIs based on the image data in the process 500 may be implemented according to a process 600 as illustrated in FIG. 6A. The VOI determination process 600 may include determining ROIs in 601, optimizing the ROIs in 603, generating a VOI in 605 and optimizing the VOI in 607.

In 601, at least two ROIs may be determined. The operation 601 may be performed by the ROI determination unit 402. In some embodiments, the at least two ROIs may include regions corresponding to the same three-dimensional target of interest in different two-dimensional slice images. For instance, a first ROI may be determined in a first two-dimensional slice image, and a second ROI may be determined in a second two-dimensional slice image. In some embodiments, the at least two ROIs may include regions of two images of interest in the same sectional plane (such as the first two-dimensional slice image and the second two-dimensional slice image). The sectional plane may include a traverse plane, a sagittal plane, a coronal plane or oblique plane with any angle. For example, with regard to a liver, a user may desire to determine a tumor in the liver, and the ROI determination unit 402 may determine tumor regions displayed in a plurality of two-dimensional slice images in sagittal plane.

The determination of ROI(s) may be performed automatically, semi-automatically or manually. In some embodiments, the ROI determination unit 402 may automatically determine an ROI according to one or more algorithms. In some embodiments, the automatic determination of the ROI may include segmenting the ROI in a plurality of two-dimensional slice images based on image characteristic information. The operation of segmenting the ROI may be performed based on one or more image segmentation algorithms. The image segmentation algorithms may include threshold segmentation, region growing, watershed segmentation, morphological segmentation algorithm, statistics segmentation, or the like, or any combination thereof. The threshold segmentation may be a segmentation algorithm based on regions. For instance, image pixels or voxels may be segmented into multiple categories by setting different characteristic threshold. According to the number of thresholds, the threshold segmentation may include a single-threshold segmentation, a multi-threshold segmentation, etc. According to differences in the algorithm principles, the threshold segmentation may include an iterative threshold segmentation, a histogram segmentation, a maximum between-cluster variance threshold segmentation, etc. The region growing algorithm may start from one or more seed points (one seed point may be a single pixel or voxel, or may be pixels or voxels within a certain small region), and combine adjacent pixels or voxels with characteristics (e.g., gray levels, textures, colors, etc.) similar to the seed point(s) for growing into a same region. Region growing may include an iterative process. For example, pixels or voxels may be added into the growing region until there may be no suitable adjacent points and the growing may be terminated. The watershed segmentation may be a process of iterative marking. The gray levels of pixels or voxels may be sorted in an ascending order, and then the pixels or voxels may be traversed in the ascending order. For each local minimum gray level, a determination may be performed on at least a portion of the pixels and voxels based on a first-in, first-out structure, and the pixels or voxels having gray levels that satisfy a pre-determined condition may be marked. Then the pixels or voxels having gray levels that satisfy the pre-determined condition may be combined with the point having the local minimum gray level to form an influence region of each local minimum gray level. A plurality of influence regions may be further combined. The morphological segmentation may be performed based on a Hessian point enhancing model, a Hessian line enhancing model, a multi-scale Gaussian template matching model, a multi-scale morphological filtering model and/or an edge-based segmentation model. The Hessian point enhancing model may be used for enhancing, for example, a circular dot graph or a quasi-circular dot graph. The Hessian line enhancing model may be used for enhancing a linear graph. The multi-scale Gaussian template matching model may be performed for segmentation based on the morphology of the target to be selected. For example, in the detection of lung nodules, the multi-scale Gaussian template matching model may be performed for segmentation based on the quasi-circular morphology of the lung nodules. The multi-scale morphological filtering model may be performed for a filtering operation on an image by using various mathematic morphology algorithms to enhance the target of interest. The edge-based segmentation model may include a segmentation model of a level set algorithm. The statistic model may include but is not limited to a Variational Expectation Maximization model, a K-means model, a Fuzzy C-means model, or the like, or any combination thereof.

In some embodiments, the determining ROIs may further include drawing ROI contour lines. In some embodiments, the ROI contour lines may be drawn based on the segmented ROIs. In some embodiments, the drawing of the ROI contour lines may be performed based on one or more curve generation algorithms. The curve generation algorithms may include a numerical differentiation algorithm, a Bresenham algorithm, a B spline curve generation algorithm, a Hermit curve generation algorithm, a Bezier curve generation algorithm, a displacement algorithm, or the like, or any combination thereof. In some embodiments, the generation of ROI contour lines may be performed based on a contour tracing algorithm. The contour tracing algorithm may include a reptile algorithm, a raster scanning algorithm, a neighborhood searching algorithm, etc. The reptile algorithm may be performed to segment a two-dimensional image into a background region and a target region (i.e., an ROI), select a point close to the boundaries of the target region as an initial point6, march by one pixel at one time, turn left in each marching after entering the target region from the background region, turn right after entering the background region from the target region, and return to the initial point after one circulation around the target region, resulting in a track as the contour line of the target region. The raster scanning algorithm may be performed to set a certain threshold and perform multiple times of row scanning and column scanning to implement tracking. The neighborhood searching algorithm may be performed to generate a neighborhood of a solution based on a neighborhood function, and then search the neighborhood of the solution for a more superior solution to replace the current solution, and trace the target contour in an iterative process.

In some embodiments, in operation 601, a user may manually determine ROIs in an image acquired in 502 or an image pre-processed in 504. For instance, a user may draw ROI contour lines manually via the interactive device 140 (e.g., a mouse). The user may draw one or more control points when manually drawing the ROI contour lines, and the system may generate a spline curve according to the control points to obtain the ROI contour lines. The ROI determination unit 402 may determine the ROIs and/or extract the characteristic information of pixels in the ROIs based on the ROI contour lines drawn manually. In some embodiments, a user may manually modify or change the ROIs determined automatically by the system.

In some embodiments, the ROI contour lines may be closed curves consisting of boundaries of the same tissue. For example, during the process of extracting liver tissue, the ROIs may include the liver tissue, and the ROI contour lines may be closed curves consisting of boundaries of the liver tissue. In some embodiments, the ROI contour lines may be closed curves including boundaries of different tissues. For instance, during the process of segmenting a liver tumor, the ROIs may include a portion of the liver tissue and tumor tissue, and the ROI contour lines may include at least two segments of non-closed curves. The at least two curves may include boundary lines of the tumor tissue and boundary lines of a portion of the liver tissue.

In 603, the determined ROIs may be optimized based on characteristic information of the image. In some embodiments, the operation of optimizing the ROIs may be performed by the editing unit 410. In some embodiments, the editing unit 410 may automatically optimize the ROIs determined in 601 based on the characteristic information of the images. The characteristic information of the images may include gray level information (e.g., grey level histogram, average grey level, the maximum or minimum grey level), texture structure, signal intensity, color saturation, contrast, luminance, or the like, or any combination thereof, associated with the two-dimensional slice images where the ROIs are located. In some embodiments, the characteristic information of the images may include the characteristic information of the pixels within the ROIs and/or the characteristic information of the pixels outside the ROIs. In some embodiments, the editing unit 410 may automatically adjust the region scope of the ROIs and/or re-draw the ROI contour lines according to the adjusted ROIs. For instance, after the ROIs are determined by the ROI determination unit 402 according to the level set algorithm, the editing unit 410 may automatically distribute the pixels having gray levels larger than a gray level threshold in the ROIs to the outside of the ROIs, so that the scope of the ROIs may be adjusted.

In some embodiments, the process of the optimization may include adjusting the scope defined by the ROI contour lines. For example, during the process of extracting a tumor, the ROI contour lines may be adjusted to allow the ROIs to include the entire tumor region as much as possible. In some embodiments, blood vessels, calcified tissue, injured tissue, or the like included in the ROIs may be excluded from the ROIs by adjusting the scope of the ROIs. In some embodiments, the ROIs may be optimized manually by a user. For instance, the user may drag the control points on the ROI contour lines via the interactive device 140 (e.g., a mouse) to adjust the scope of the ROIs. The selection of the control points may be based on the characteristic information of the images observed by the user (e.g., gray level information).

In 605, a VOI may be generated based on the ROIs. In some embodiments, the operation of generating the VOI may be performed by the VOI generation unit 404. The generation of the VOI may be performed based on the at least two ROIs determined in 601, or the ROIs optimized in 603. In some embodiments, the process of generating the VOI may include generating a contour surface of the VOI. The contour surface of the VOI may be generated based on the ROI contour lines. The generation of VOI contour surface based on ROI contour lines may be performed based on any one or more curved surface reconstruction techniques described in the present disclosure.

In some embodiments, the VOI contour surface may be a three-dimensional mask image. The three-dimensional mask image may refer to an image in which the gray level of pixels on or inside the VOI contour surface is 1, and the gray level of pixels outside the VOI contour surface is 0, vice versa. Furthermore, an extraction operation of characteristic information (e.g., an extraction of gray level information of the VOI) may be conducted on voxels of the VOI based on the mask image. For example, the gray level of the mask image of the VOI contour surface may be multiplied with the gray levels of corresponding voxels in volume data (e.g., image data including characteristic information of voxels). As a result, the grey level information of voxels within the VOI may remain unchanged, while the gray level information of voxels outside the VOI may be 0, and thus the gray level information of voxels in the VOI may be extracted. It should be noted that the corresponding voxels may refer to voxels of the target of interest displayed in volume data corresponding to the same physical position of the voxels in the mask image. In some embodiments, the VOI contour surface may be displayed in the form of a three-dimensional mesh.

In 607, the generated VOI may be optimized based on characteristic information of the images. In some embodiments, the operation of optimizing the generated VOI may be performed by the editing unit 410. In some embodiments, the editing unit 410 may automatically optimize the VOI according to the characteristic information of the images. The characteristic information of the images may include gray level information (e.g., grey level histogram, average grey level, the maximum or minimum grey level), texture structure, signal intensity, color saturation, contrast, luminance, or the like, or any combination thereof. In some embodiments, the characteristic information of the images may include the characteristic information of the voxels within the VOI and/or the characteristic information of the voxels outside the VOI. In some embodiments, the process of optimization may include adjusting the volume scope included by the VOI contour surface. For example, during the process of extracting a tumor, the scope of the VOI contour surface may be adjusted to allow the VOI to include the entire tumor region as much as possible. In some embodiments, blood vessels, calcified tissue, injured tissue, or the like included in the VOI may be excluded from the VOI by adjusting the scope of the VOI. In some embodiments, the optimization of the VOI may be performed based on manual optimization by a user, or may be implemented by automatic optimization. For instance, the user may drag the point(s) on the VOI contour surface via the interactive device 140 (e.g., a mouse) to adjust the scope of the VOI. As another example, a gray level threshold may be set based on the gray level information of voxels in the VOI, and the editing unit 410 may automatically distribute the voxels having gray levels larger than the gray level threshold in the VOI to the outside of the VOI, so that the scope of the VOI may be adjusted.

It should be noted that the above descriptions of the process 600 of determining a VOI are only for the convenience of illustration, and not intended to limit the present disclosure to the scope of the exemplary embodiments. It should be understand that for those skilled in the art, after understanding the principles of the system and method, modifications may be conducted on the process 600 of determining a VOI, without departing from the principles. In some embodiments, operations 603 and/or 607 may be omitted from the process 600 of determining the VOI. In some embodiments, operations 601 and 603 may be combined into one operation. For instance, the ROI determination unit 402 may determine an ROI based on the characteristic information of the image(s) without an extra optimization operation for the ROIs. In some embodiments, operations 605 and 607 may be combined into one operation. For instance, the VOI generation unit 404 may generate a VOI based on the characteristic information of the image(s) without an extra optimization operation for the VOI. Similar variations fall within the protection scope of the present disclosure.

Figure 6B:
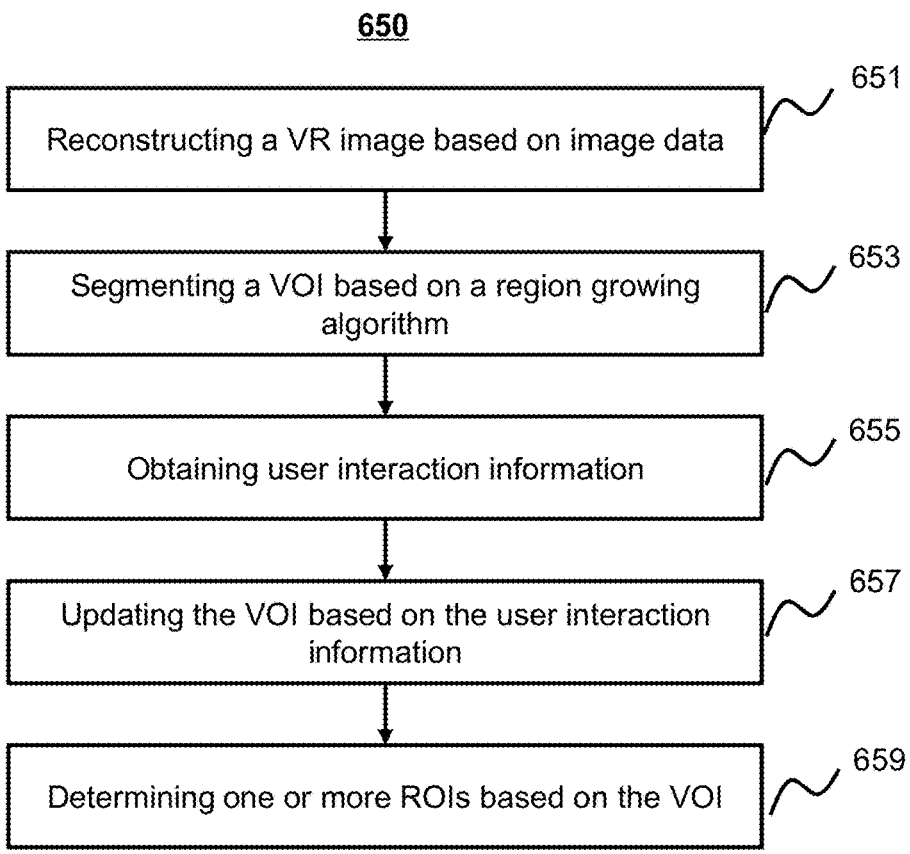
FIG. 6B is a flowchart of an exemplary process for determining a VOI and/or an ROI according to some embodiments of the present disclosure.

FIG. 6B is a flowchart of an exemplary process for determining a VOI and/or an ROI according to some embodiments of the present disclosure. In some embodiments, the operation 506 of determining a VOI based on image data in the process 500 may be implemented according to the process 650 as illustrated in FIG. 6B.

In 651, a volume rendering (VR) image may be reconstructed based on image data. In some embodiments, operation 651 may be performed by the pre-processing module 304. In some embodiments, the image data may be the image data acquired in operation 502, including two-dimensional slice image data and/or three-dimensional slice image data. In 651, volume rendering techniques (VRT) may be used to composite a plurality of two-dimensional images to a three-dimensional stereo image, and set the CT values of the voxels of the three-dimensional stereo image as different transparencies that varies from completely opaque to completely transparent. Meanwhile, the three-dimensional stereo image may be displayed with different gray scales (or pseudo colors) using a virtual illumination effect. For example, in the reconstruction process of a VR image of head and neck, the transparency of skull tissue is relatively low, while the transparency of blood vessel tissue is relatively high, and thus the gray scales (or pseudo colors) of the skull and blood vessels displayed in the VR image may be different. In some embodiments, in the reconstruction of the VR image, a virtual projection ray may pass the image data by a pre-determined angle, the pixels or voxels in different slice images of the image data (e.g., multiple two-dimensional slice images) on the projection line may be projected, and the information of pixels or voxels in different two-dimensional slice images may be comprehensively displayed.

In 653, a VOI may be segmented based on a region growing algorithm. In some embodiments, the operation of VOI region growing may be performed by the VOI generation unit 404. In some embodiments, the VOI region growing may be performed based on the VR image. For instance, the region growing algorithm may include selecting at least one seed point as the initial point for growing based on the VR image; combining neighborhood voxels around the seed point to the region where the seed point is located, wherein the voxels to be combined have the same characteristics as or similar characteristics to the seed point; determining the growing voxels as seed points and continue growing around until no voxels that satisfy a predetermined condition may be found and then the growing process may be terminated. In some embodiments, the seed point may include one voxel or a region including a plurality of voxels. In some embodiments, the similar characteristics of the voxels or pixels may include texture, gray level, average gray level, signal intensity, color saturation, contrast, luminance, or the like, or any combination thereof. In some embodiments, in the process of region growing, a continuous dynamic process of the VOI growing may be observed based on the changes of newly added seed points. For example, for the region growing of blood vessel tissue, a user may perform the growing of blood vessel tissue based on a VR image, and observe the changing process of the growing of the blood vessel tissue, such as whether the growing is overflowed/incomplete or not.

In some embodiments, the region growing of the VOI may be performed based on image data. This may indicate that operation 651 may be performed after 653. For instance, at least one seed point in a two-dimensional slice image may be selected as the initial point for growing; neighborhood voxels around the seed point may be combined in the region where the seed point is located, wherein the voxels to be combined have the same characteristics as or similar characteristics to the seed point; the growing voxels may be determined as new seed points, and growing process may proceed until no voxels that satisfy a predetermined condition may be found and then the growing process may be terminated; and then a VR image of the VOI may be reconstructed based on the VOI obtained through region growing and the volume rendering technique.

In 655, user interaction information may be obtained. In some embodiments, the operation 655 may be performed by the interactive device 140. The interactive information may include rotating an image, scaling an image, translating an image, suspending region growing, stop region growing, or the like, or any combination thereof. In some embodiments, the user interactive information may include stop region growing after suspending region growing. In some embodiments, a user may perform the interactive operations by the interactive device 140 (e.g., a mouse).

In 657, the VOI may be updated based on the user interactive information. In some embodiments, the operation of 657 may be performed by the VOI generation unit 404 and/or the updating unit 412. The user interactive information may suspend the process of the region growing. In some embodiments, in 657, at least a portion of the VOI may be displayed. For instance, in a VR image, there may be a masking relationship between the growing VOI (e.g., blood vessels) and other tissue (e.g., skeletons). During the process of region growing, a user may observe the entire VOI formed by region growing, but may not be able to observe the portion of VOI covered by other tissue. The portion of VOI that is not covered by other tissue may be displayed when the region growing is suspended, and thus it may be convenient for a user to observe the masking relationship between the VOI and other tissue. For example, during the growing process of blood vessel tissue of head and neck, newly growing blood vessels may be displayed through a VR image so that it may be convenient for the user to observe the changes in the growing process. In the process of region growing, in order to observe the masking relationship between the currently growing blood vessels and the skull, a user may rotate the region of growing and observe the masking relationship of the growing blood vessels and the skull. In some embodiments, the speed of region growing may be controlled based on the user interaction information. In some embodiments, the speed of region growing may be controlled based on the extraction frequency of seed points. For instance, for a relatively small VOI, the time required for region growing may be relatively short. For the relatively small VOI, the extraction frequency of seed points during region growing may be relatively large, and the speed of region growing may be relatively high. However, a user may desire to have enough time to observe the growing process of the relatively small VOI, and thus the speed of region growing may be decreased by decreasing the extraction frequency of seed points. As another example, for a relatively large VOI, the time required for region growing may be relatively long. For the relatively large VOI, the extraction frequency of seed points during the early stage of region growing may be relatively small. However, as the seed points increase, the number of seed points extracted in each growing may increase fast. In the late stage of region growing, the growing may be excessively fast and may easily overflow. Thus the user may desire that the region growing process for the relatively large VOI may be completed fast and the speed of region growing in the late stage may be stable. Therefore, in the early stage of region growing, the extraction frequency of seed points may be increased so as to increase the speed of region growing in the early stage, while in the late stage of region growing, the extraction frequency of seed points may be decreased so as to decrease the speed of region growing and cause the speed of region growing to tend to be stable.

In 659, one or more ROIs may be determined based on the VOI. In some embodiments, the operation 659 may be performed by the ROI determination unit 402. In some embodiments, the VOI may be the dynamically changing VOI during the process of region growing, or may be the generated portion of a VOI when the region growing is suspended. In some embodiments, in 659, slice processing may be performed on the VOI to obtain two-dimensional slice images. The VOI may be marked in the two-dimensional slice images and displayed as ROIs. In some embodiments, in 659, the ROIs may be displayed synchronously in an MPR window when the VOI is displayed in a VR window.

It should be noted that the above descriptions of the process 650 are only for the convenience of illustration, and not intended to limit the present disclosure to the scope of the exemplary embodiments. It should be understand that for those skilled in the art, after understanding the principles of the present disclosure, various modifications may be conducted without departing from the principles. For instance, operations 655, 657 and/or 659 may be omitted from the process 650. In some embodiments, the process 650 may include pre-processing the image data. Similar variations fall within the protection of the present disclosure.

Figure 7:
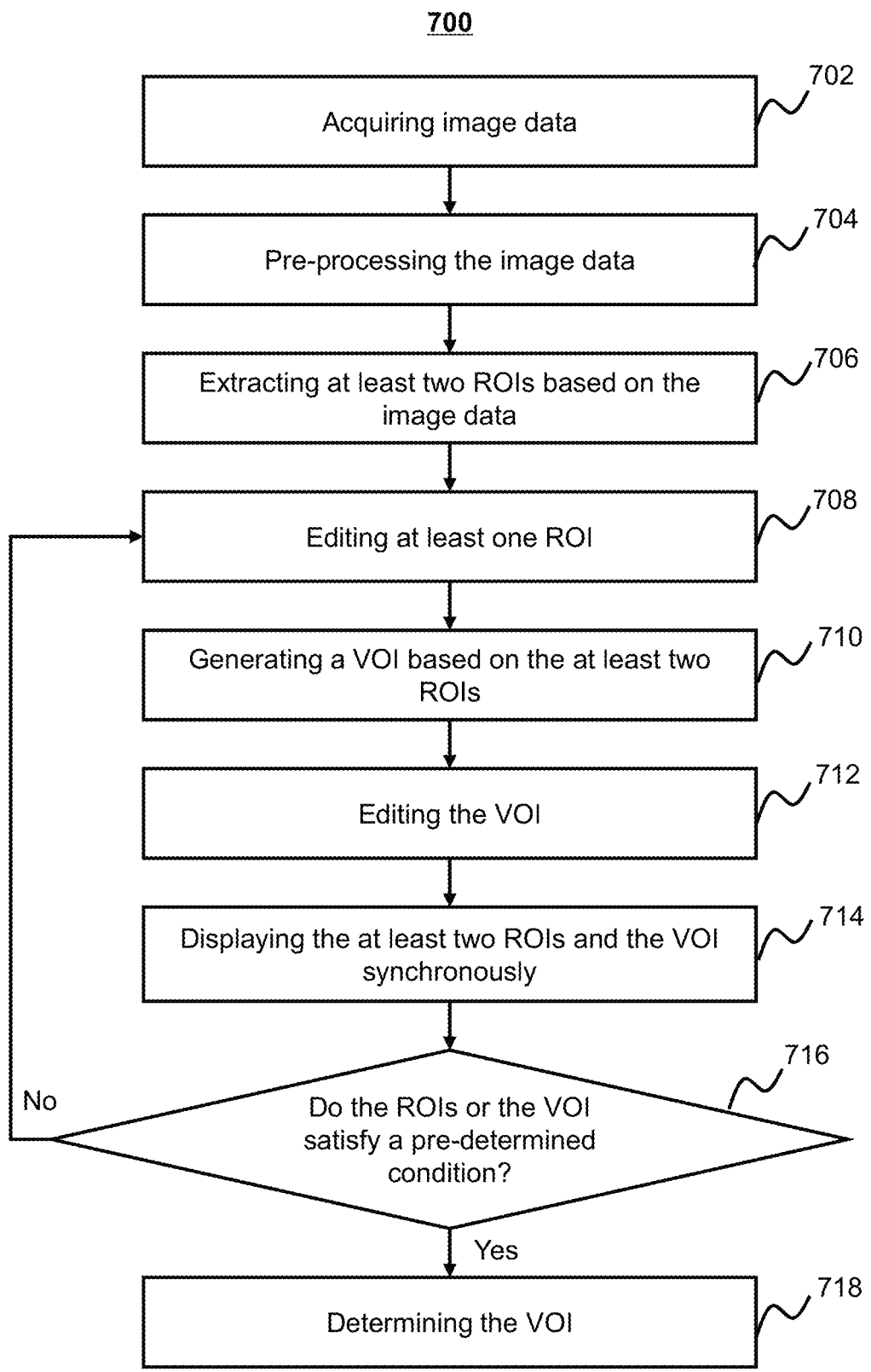
FIG. 7 is a flowchart of an exemplary process for determining a VOI according to some embodiments of the present disclosure.

FIG. 7 is a flowchart of an exemplary process for determining a VOI according to some embodiments of the present disclosure.

In 702, image data may be acquired. Operation 702 may be performed by the image data acquisition module 302. In some embodiments, the image data may be traverse plane image data, coronal plane image data, sagittal plane image data or oblique plane image data. The image data may include at least two slices of the two-dimensional slice images. In some embodiments, more descriptions of the acquisition of the image data may be found elsewhere in the present disclosure (e.g., FIG. 5 and descriptions thereof).

In 704, the image data may be pre-processed. Operation 704 may be performed by the pre-processing module 304. In some embodiments, the pre-processing may include a pre-processing operation performed on any slice of the two-dimensional slice images. In some embodiments, the pre-processing may include a pre-processing operation (e.g., interpolation processing) performed on the at least two slices of the two-dimensional slice images. In some embodiments, more descriptions of the pre-processing of the image data may be found elsewhere in the present disclosure (e.g., FIG. 5 and descriptions thereof).

In 706, at least two ROIs may be extracted based on the image data. Operation 706 may be performed by the ROI determination unit 402. The image data may be the image data acquired in 702 or the image data pre-processed in 704. In some embodiments, the at least two ROIs may be located in different slices of the two-dimensional slice images. In some embodiments, 706 may extract the characteristic information of the at least two ROIs (i.e., ROI segmentation) and/or extract the at least two ROIs. In some embodiments, contour lines of the at least two ROIs may be drawn according to any curve generation algorithm described in the present disclosure.

In 708, at least one ROI may be edited. Operation 708 may be performed by the editing unit 410. In some embodiments, the editing at least one ROI may include adjusting the scope of the ROI based on characteristic information of the image(s). In some embodiments, at least two control points may be extracted based on one ROI extracted in 706. The control points may be key points or high curvature points on an ROI contour line that determine the shape of the contour line. The curve generation unit 406 may generate a spline curve by an interpolation operation on the control points. Then the editing unit 410 may edit the control points and cause the spline curve generated based on the control points to coincide with the ROI contour line as much as possible. In some embodiments, the ROI may be redetermined based on a spline curve generated based on the edited control points. In some embodiments, the extraction algorithms of the control points may include a polygon approximation algorithm based on splitting and mergence, a polygon approximation algorithm based on area error, etc. The polygon approximation algorithm based on splitting and mergence may start from a polygon corresponding to an original contour line of the ROI and repetitively perform an iteration process of splitting and mergence on a segmental arc that is to be segmented. The process may start at a point on an original segmental arc that may serve as a division point. The original segmental arc may be segmented into two segmental arcs, and the division point may become a new vertex of an approximate polygon. Meanwhile, one side of the original approximate polygon may be removed and a new side may be added. The operation of splitting and mergence may be repetitively performed on the upper portion and the bottom portion of the segmental arcs, and thus characteristic points on the boundary lines of the top border and characteristic points on the boundary lines of the bottom border may be obtained. The polygon approximation algorithm based on area error may use the influence extent of each pixel of the original contour line on the regional area included by the entire original contour line as weight, gradually remove the pixels/voxels having a relatively small influence on the change of the area, keep the pixels/voxels having a relatively apparent influence on the change of the area, and finally cause the area error to satisfy a certain error threshold. The pixels/voxels having a relatively apparent influence on the change of the area may serve as control points. In some embodiments, the editing unit 410 may determine whether a difference between the regional area included by the original contour line and the regional area included by the contour line re-generated after the removal of a pixel/voxel is less than a pre-determined value. If the difference associated with the regional area is less than the pre-determined value, the pixel/voxel may be determined as a point having a relatively small influence on the change of the area.

In 710, a VOI may be generated based on the at least two ROIs. Operation 710 may be performed by the VOI generation unit 404. In some embodiments, the at least two ROIs may be the ROIs determined in 706 or the ROIs edited in 708. In some embodiments, the VOI may be generated according to any volume rendering algorithm described in the present disclosure. For instance, characteristic information of voxels in the VOI may be generated by performing an interpolation operation on the characteristic information of pixels in the at least two ROIs, and the VOI may be extracted based on the generated characteristic information of voxels in the VOI. In some embodiments, the VOI may be generated according to any surface rendering algorithm described in the present disclosure. For example, contour surface(s) of the VOI may be generated by performing an interpolation operation on the contour lines of the at least two ROIs, and the VOI may be extracted based on the contour surface(s) of the VOI.

In 712, the VOI may be edited. Operation 712 may be performed by the editing unit 410. In some embodiments, the scope of the VOI may be adjusted based on image characteristic information (e.g., gray levels of pixels or voxels) in 712. For instance, through setting a gray level threshold, the voxels that have larger gray level values than the gray level threshold may be determined to belong the outside of the scope of the VOI. In some embodiments, one or more ROIs in the VOI may be edited. For example, the scope of the ROIs may be adjusted by editing the control points of the ROIs, and then the VOI may be re-generated based on the edited ROIs.

In 714, the at least two ROIs and the VOI may be displayed synchronously. Operation 714 may be performed by the display module 310. In some embodiments, images in different sectional planes (e.g., images in the traverse plane, the coronal plane and the sagittal plane) of the same ROI may be displayed simultaneously in the same two-dimensional and/or three-dimensional display window in 714. In some embodiments, ROI images in different sectional planes corresponding to the same VOI (e.g., ROI images in the traverse plane, the coronal plane and the sagittal plane corresponding to the same VOI) may be displayed simultaneously in the same two-dimensional and/or three-dimensional display window in 714. In some embodiments, the two dimensional display window may be an MPR view window. The three-dimensional display window may be a volume rendering view window. In some embodiments, in 714, the VOI and the ROI(s) may be displayed simultaneously in the three-dimensional window. In 714, the sectional planes where the ROI(s) are located may be determined in the VOI, and the ROI(s) may be marked and/or displayed. In some embodiments, the display may be performed in real time. In some embodiments, 714 may be performed simultaneously with any of 706, 708, 710, 712, etc. For example, if the operation 706 is being performed (e.g., if a user is rendering two-dimensional ROI(s)), the display module 310 may position the drawn ROI contour line(s) in the three-dimensional VOI in real time, and/or mark (and/or display) the ROI(s) in the three-dimensional VOI. If the number of the rendered ROI slices reaches two, the display module 310 may automatically display the three-dimensional VOI generated according to the currently rendered two-dimensional ROI(s) in the three-dimensional display window. In some embodiments, the display may not be performed in real time. For example, after a user has completed the rendering of a plurality of ROIs in a plurality of two-dimensional slice images, the display module 310 may display the VOI generated based on the plurality of ROIs in the three-dimensional display window.

In 716, whether the ROI(s) or the VOI satisfy a pre-determined condition may be judged. Operation 716 may be performed by the judgment unit 414. In some embodiments, the pre-determined condition may relate to a fact that the ROIs or the VOI do not include at least a portion of blood vessels, calcified tissue or injured tissue, etc. If the ROIs or the VOI satisfy the pre-determined condition (e.g., the ROIs or the VOI do not include at least a portion of blood vessels, calcified tissue or injured tissue), then operation 718 may be perform; if the ROIs or the VOI do not satisfy the predetermined condition, then the process 700 may return to 708 and continue to edit at least one ROI. In some embodiments, the judgment unit 414 may judge whether the ROIs or the VOI satisfy the pre-determined condition based on characteristic information of the ROIs or the VOI. For instance, the judgment unit 414 may judge whether the gray level values of all the pixels or voxels in the ROIs or the VOI are less than a pre-determined gray level threshold. If the gray level values of all the pixels or voxels are less than the pre-determined gray level threshold, then the ROIs or the VOI may not satisfy the pre-determined condition; if the gray level values of at least a portion of the pixels or voxels are larger than the pre-determined gray level threshold, then the ROIs or the VOI may satisfy the pre-determined condition.

In 718, the VOI may be determined. Operation 718 may be performed by the VOI determination module 306. In some embodiments, in 718, the characteristic information of voxels in the VOI may be extracted, the characteristic information of pixels in the ROIs may be extracted, and/or the contour surface(s) of the VOI may be determined.

It should be noted that the above descriptions of the process 700 for determining a VOI are only for the convenience of illustration, and not intended to limit the present disclosure to the scope of the exemplary embodiments. It should be understand that for those skilled in the art, after understanding the principles of the present disclosure, various modifications may be conducted to the process 700 for determining a VOI without departing from the principles. For example, operations 704 and/or 708 may be omitted from the process 700 for determining a VOI. Similar variations fall within the protection scope of the present disclosure.

Figure 8:
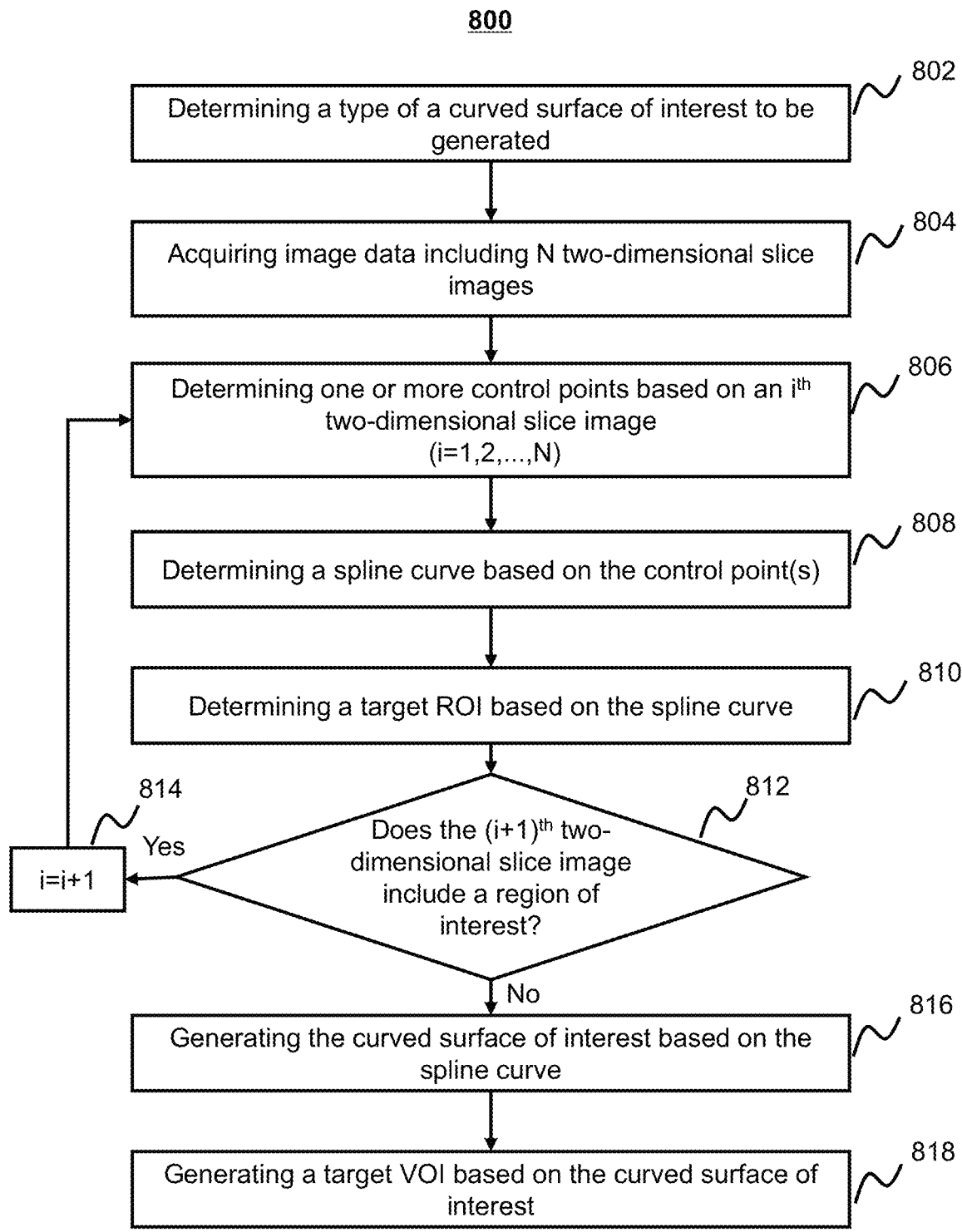
FIG. 8 is a flowchart of an exemplary process for generating a curved surface according to some embodiments of the present disclosure.

FIG. 8 is a flowchart of an exemplary process for generating a curved surface according to some embodiments of the present disclosure. In some embodiments, the operation 710 of generating a VOI based on ROIs in the process 700 may be according to the process 800 as illustrated in FIG. 8. In operation 802, a type of a curved surface of interest to be generated may be determined. Operation 802 may be implemented by the curved surface generation unit 408. In some embodiments, the curved surface of interest may be a closed curved surface. The closed curved surface may be generated based on a two-dimensional slice image in a traverse plane, a sagittal plane, a coronal plane or an opaque plane of any angle. In some embodiments, the curved surface of interest may be a non-closed curved surface. The non-closed curved surface may segment the target of interest into at least two portions. In some embodiments, the type of the curved surface of interest may be determined in 802 according to a division scheme. The division scheme may include diving the target of interest into different portions such as top and bottom portions, left and right portions, front and back portions or any other orientations. The top and bottom portions, left and right portions, front and back portions or other orientations may be determined based on the direction of the front view of the target of interest. For instance, a portion close to the head of an object may be the top portion; a portion close to the feet of the object may be the bottom portion; a portion close to the left of the object may be the left portion; a portion close to the right of the object may be the right portion; a portion close to the front chest of the object may be the front portion, a portion close to the back of the object may be the back portion. If the target of interest is segmented into top and bottom portions, the curved surface of interest may use the direction in a traverse plane as a reference, and the generation of the curved surface of interest may be performed based on two-dimensional image(s) in a sagittal plane or a coronal plane. If the target of interest is segmented into left and right portions or front and back portions, the curved surface of interest may use the direction in a sagittal plane or a coronal plane as a reference, and the generation of the curved surface of interest may be performed based on two-dimensional image(s) in a traverse plane.

In 804, image data may be acquired. The image data may include N two-dimensional slice images, wherein N may be an integer larger than 0. Operation 804 may be implemented by the image data acquisition module 302. In some embodiments, at least one of the N slice images may include the target of interest. A displayed region of the target of interest in a certain two-dimensional sectional slice image may be considered as an ROI. In some embodiments, the acquisition of the image data may be performed based on the type of the curved surface determined in 802. For example, if the curved surface segments the target of interest into top and bottom portions, then the image may be a two-dimensional slice image in a sagittal plane or a coronal plane. If the curved surface segments the target of interest into front and back portions or left and right portions, then the image may be a two-dimensional slice image in a traverse plane.

In 806, one or more control points may be determined based on an $i^{th}$ two dimensional slice image, wherein i may be a positive integer less than or equal to N (i.e., ON). Operation 806 may be implemented by the curve generation unit 406. In some embodiments, the $i^{th}$ two dimensional slice image may be pre-processed in 806. In 806, an initial segmentation of an ROI may be performed on the two-dimensional slice image or the pre-processed two-dimensional slice image to obtain an original ROI. The original ROI may include at least one portion of the target of interest. The initial segmentation may be performed based on one or more segmentation algorithms described in the present disclosure. In 806, an original ROI contour line may be drawn manually or automatically based on the boundary of the original ROI, and/or the control points may be determined based on the gray level information of pixels in the original ROI. In some embodiments, the control points may include characteristic points located on or around the original ROI contour line (or the boundary) or characteristic points located within the original ROI. The characteristic points may be key points or high curvature points located on the contour line (or the boundary) representing the original ROI or the division line(s) of different regions in the original ROI, and the key points or high curvature points may determine the shape of the contour line (or the division line).

In some embodiments, extraction algorithms of the characteristic points may be implemented using point probe operator(s), for example, a template matching algorithm, a geometrical characteristic detection algorithm, etc. The template matching algorithm may set a series of templates for characteristic points (e.g., angular points, cross points, etc.) and judge whether the pixel(s) located in the center of sub-windows are characteristic points according to the similarity of the templates and all the image sub-windows. The geometrical characteristic detection algorithm may include an extraction algorithm based on boundary curvatures, an extraction algorithm based on gray level information of an image, etc. In some embodiments, the point probe operators may include Harris operator, Forstner operator, Susan operator, MIC operator, Moravec operator, SIFT operator, or the like, or any combination thereof.

In 808, a spline curve may be determined based on the control points. Operation 808 may be performed by the curve generation unit 406. In some embodiments, the control points may be processed based on an interpolation algorithm to generate the spline curve. The interpolation algorithm may include a smooth interpolation with unequal intervals, a nearest-neighbor interpolation algorithm, a bilinear interpolation algorithm, a bicubic gray-level interpolation algorithm, a space-variant linear gray-level interpolation algorithm, a fractal interpolation algorithm, or the like, or any combination thereof.

Figure 10A:
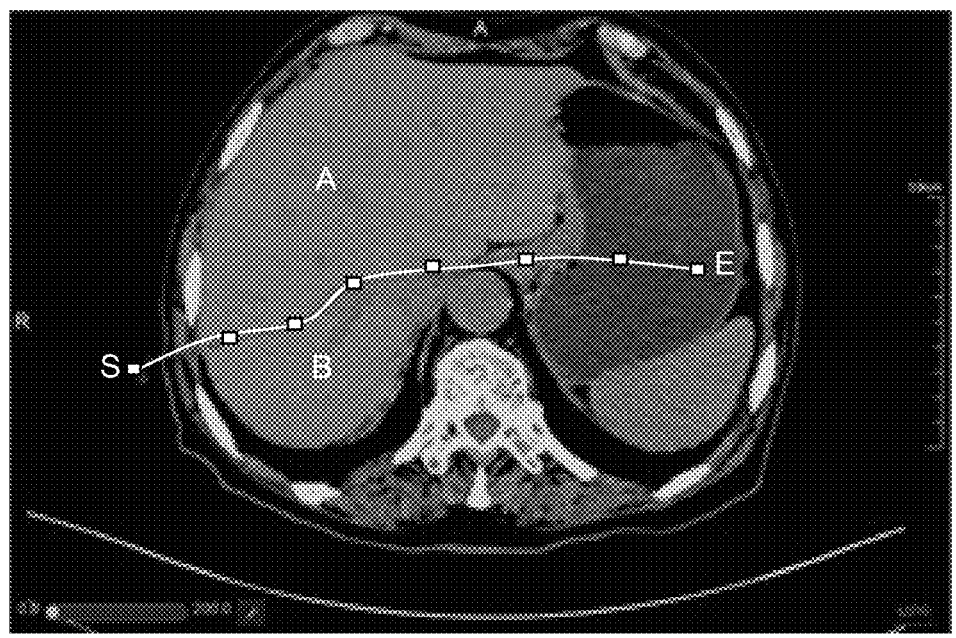
FIGS. 10A and 10B are schematic diagrams of an exemplary spline curve according to some embodiments of the present disclosure.

In some embodiments, the spline curve may be a closed curve. The closed curve may include at least a portion of the original ROI. For instance, if a liver image is processed, the spline curve may be a boundary line of liver tissue to distinguish liver tissue and non-liver tissue. In some embodiments, the spline curve may be a non-closed curve (such as the spline curve SE as illustrated in FIG. 10A or The non-closed curve may segment the original ROI into at least two portions. Further, the non-closed curve and a portion of the contour line of the original ROI may form a closed curve, and the closed curve may include a target of interest. As illustrated in FIG. 10A, the closed curve formed by the spline curve SE and the bottom boundary of the region B may determine a certain segment of the liver (as illustrated by the region B).

In 810, a target ROI may be determined based on the spline curve. Operation 810 may be performed by the ROI determination unit 402. In some embodiments, the target ROI may include at least a portion of the original ROI. In some embodiments, the scope of the target ROI may be adjusted based on the control points on the spline curve. For example, a user may adjust the spline curve by manually dragging the control point(s) to other position(s) so as to adjust the scope of the target ROI. In some embodiments, the target ROI may also be adjusted based on image characteristic information. For instance, a gray level threshold may be set and used to remove pixel(s) in the target ROI that have larger or smaller gray level values than the gray level threshold.

In 812, whether the $(i+1)^{th}$ two-dimensional slice image includes a region of interest may be judged. Operation 812 may be performed by the judgment unit 414. The ROI may refer to the displayed region of the target of interest in the $(i+1)^{th}$ two-dimensional slice image. If the $(i+1)^{th}$ two-dimensional slice image includes the ROI, then operation 814 may be performed, and operation 806 may be performed based on the $(i+1)^{th}$ two-dimensional slice image. If the $(i+1)^{th}$ two-dimensional slice image does not include the ROI, then operation 816 may be performed. In some embodiments, the judgment may be performed by a user through observing the image displayed in a two-dimensional display window in 812. In some embodiments, the judgment may be automatically performed according to image characteristic information. For instance, whether the $(i+1)^{th}$ two-dimensional slice image includes the ROI may be judged by comparing the gray level information of the $(i+1)^{th}$ two-dimensional slice image and the $i^{th}$ two-dimensional slice image.

In 816, the curved surface of interest may be generated based on the spline curve. Operation 816 may be performed by the curved surface generation unit 408. In some embodiments, if the spline curve is a closed curve, then the curved surface of interest may be a closed curved surface. The closed curved surface may be a VOI contour surface. In some embodiments, if the spline curve is a non-closed curve, then the curved surface of interest may be a non-closed curved surface. In some embodiments, the non-closed curved surface may segment the VOI into at least two portions. In some embodiments, the curved surface of interest may be a two-dimensional or three-dimensional mask image. In some embodiments, the curved surface of interest may be displayed in the form of a mesh. In some embodiments, in 816, the spline curve and the control points may be displayed in a two-dimensional display window, the curved surface of interest may be displayed synchronously in a three-dimensional display window, and/or the spline curve and the control points may be marked (and/or displayed) in the curved surface of interest.

In 818, a target VOI may be generated based on the curved surface of interest. Operation 818 may be performed by the VOI generation unit 404. In some embodiments, if the curved surface of interest is a closed curved surface, then the characteristic information of voxels in the target VOI may be extracted according to the closed curved surface in 818. In some embodiments, if the curved surface of interest is a non-closed curved surface, then in 818, an original VOI generated by an initial segmentation may be segmented into at least two portions according to the non-closed curved surface. The original VOI may be obtained by an initial segmentation of image data performed in any of operations 808 through 818. The non-closed curved surface and a portion of the original VOI contour surface may form a closed curved surface, i.e., the contour surface of the target VOI. In some embodiments, the target VOI may be certain tissue or an organ or a portion thereof, for example, a liver, a certain segment of tissue in a liver or a tumor in a liver, etc.

It should be noted that the above descriptions of the process 800 for generating a curved surface are only for the convenience of illustration, and not intended to limit the present disclosure to the scope of the exemplary embodiments. It should be understand that for those skilled in the art, after understanding the principles of the present disclosure, various modifications may be conducted to the process 800 for generating a curved surface without departing from the principles. The foregoing or following operations may not necessarily be performed according to the describe order. On the contrary, various operations may be performed simultaneously or in a reverse order. Meanwhile, other operations may be added into the process or one or more operations of operations may be removed from the process. For example, operation 804 may be performed first, then operation 802 may be performed, or operations 802 and 804 may be performed simultaneously. As another example, the process 800 for generating a curved surface may further include pre-processing the acquired image data. Similar variations fall within the protection scope of the present disclosure.

Figure 9:
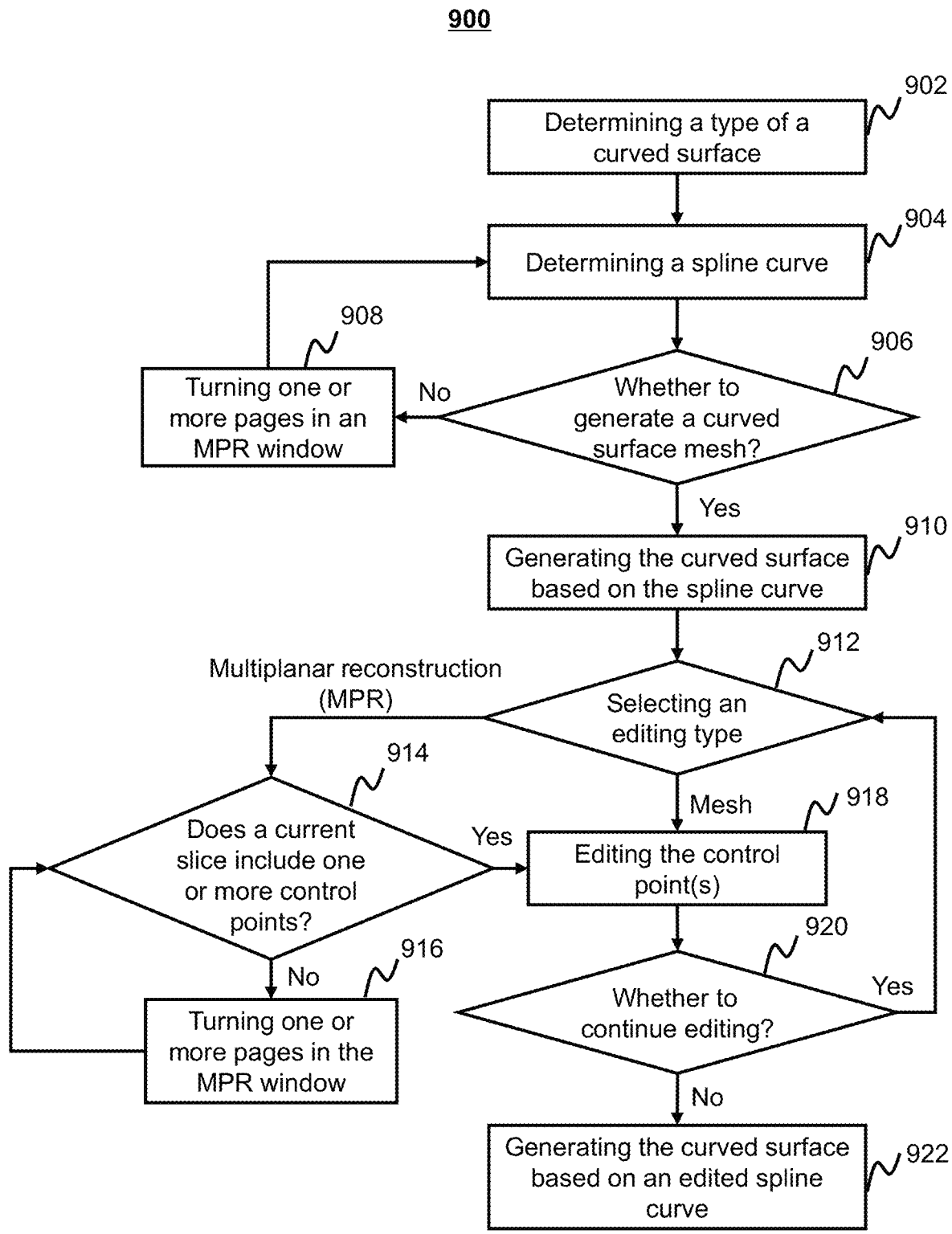
FIG. 9 is a flowchart of an exemplary process for generating and editing a curved surface in a multiplanar reconstruction window and/or a volume rendering window according to some embodiments of the present disclosure.

FIG. 9 is a flowchart of an exemplary process for generating and editing a curved surface in a multiplanar reconstruction window and/or a volume rendering window according to some embodiments of the present disclosure. In some embodiments, the operation 708 of editing at least one ROI and/or the operation 710 of generating a VOI based on the ROI(s) in the process 700 may be implemented according to the process 900 as illustrated in FIG. 9.

In 902, a type of a curved surface may be determined. Operation 902 may be performed by the curved surface generation unit 408. In some embodiments, for different types of curved surface, spline curves may be drawn in image view windows of different sectional planes. The determination of the type of a curved surface may be performed based on the function of the curved surface. For example, if the curved surface is used to segment the target of interest into front and back portions or left and right portions, the spline curve(s) may need to be drawn in an MPR window of a traverse plane. As another example, if the curved surface is used to segment the target of interest into upper and bottom portions, then the spline curve(s) may need to be drawn in an MPR window of a coronal plane or a sagittal plane. More descriptions of the determination of the type of the curved surface may be found elsewhere in the present disclosure (e.g., FIG. 8 and descriptions thereof).

In 904, one or more spline curves may be determined. Operation 904 may be performed by the curve generation unit 406. The spline curve(s) may be drawn based on two-dimensional slice image(s) displayed in an MPR window of one or more sectional planes. In some embodiments, in 904, at least one control point may be determined based on the target of interest in a two-dimensional slice image, and a spline curve may be generated based on the at least one control point. Similarly, a plurality of spline curves may be determined in a plurality of two-dimensional slice images in 904. In some embodiments, the spline curves may be contour lines of the target of interest. In some embodiments, the spline curve may be a segmentation line for different regions in the target of interest, and the segmentation line may segment the target of interest into at least two portions. In some embodiments, a list of spline curves including a plurality of spline curves in a plurality of two-dimensional slice images may be generated. The list of spline curves may include at least two spline curves. More descriptions of the selection of control points and the determination of the spline curves may be found elsewhere in the present disclosure (e.g., FIG. 8 and the descriptions thereof).

In 906, whether to generate a curved surface mesh may be judged. Operation 906 may be performed by the judgment unit 414. In some embodiments, whether to generate a curved surface mesh may be judged according to user requirement(s). For instance, a user may set a number threshold for the spline curves, and the judgment unit 414 may judge whether the number of spline curves determined in 904 is larger than the threshold. If the number of the spline curves is larger than the threshold, then in 906, the judgment result may be that a curved surface mesh may be generated. In some embodiments, in 906, whether to generate a curved surface mesh may be judged based on whether the current two-dimensional slice image includes the target of interest. In some embodiments, a user may observe whether the current two-dimensional image includes the target of interest in an MPR window. The user may input instruction(s) via the interactive device 140 (e.g., a keyboard, a mouse, etc.) based on the observation result, and the judgment unit 414 may judge whether to generate a curved surface mesh based on the inputted instructions. In some embodiments, whether the current two-dimensional slice image includes the target of interest may be automatically judged based on gray level information of the image. For instance, in 906, the gray level information of the target of interest may be compared with the gray level information of the current two-dimensional slice image to judge whether the current two-dimensional slice image includes the target of interest. If it is determined to generate the curved surface mesh, then operation 910 may be performed. If it is determined not to generate the curved surface mesh, then operation 908 may be performed. In 908, one or more pages may be turned in an MPR window to obtain a next two-dimensional slice image. After the operation 908, the process 900 may return to 904 and continue to determine a spline curve.

In 910, the curved surface may be generated based on the spline curve. Operation 910 may be performed by the curved surface generation unit 408. In some embodiments, the generation of the curved surface may be performed using any curved surface reconstruction technique described in the present disclosure. In some embodiments, the curved surface may be a mask image. In some embodiments, the curved surface may be displayed in the form of a mesh. In some embodiments, the spline curve may be displayed in an MPR window, and the generated curved surface may be displayed simultaneously in a volume rendering window. In some embodiments, at least one spline curve and/or the control points on the spline curve may be marked on the curved surface and displayed.

In 912, an editing type may be determined. Operation 912 may be performed by the editing unit 410. The editing type may refer to the type of a display window. The editing type may include editing the spline curve in an MPR window or editing the spline curve in a volume rendering window (i.e., the curved surface mesh). The editing type may be selected by a user, or the system may automatically select a default editing type. If an MPR window is selected for editing the spline curve, then operation 914 may be performed; if a volume rendering window is selected for editing the spline curve, then operation 918 may be performed.

In 914, whether the current two-dimensional slice image displayed in the MPR window includes control points may be determined. Operation 914 may be performed by the judgment unit 414. If the current two-dimensional slice image does not include control points, then 916 may be performed to turn one or more pages in the MPR window, and the judgment may be performed on the next two-dimensional slice image. If the current two-dimensional slice image includes control points, then operation 918 may be performed.

In 918, the control point(s) may be edited. Operation 918 may be performed by the editing unit 410. The control points may be edited in the MPR window and/or the volume rendering window or the mesh rendering window. In some embodiments, a user may implement the editing of the control point(s) by dragging the control point(s) via the interactive device 140 (e.g., a mouse). In some embodiments, if the control point(s) are edited in the MPR window, then the spline curve displayed in the MPR window and/or the curved surface displayed in the volume rendering window may be updated synchronously according to the edited control point(s). If the control points are edited in the volume rendering window or mesh rendering window, then the curved surface displayed in the volume rendering window may be updated synchronously according to the edited control point(s), and the spline curve where the control points are located may be updated synchronously in the MPR window. For instance, in the volume rendering window or the mesh rendering window, a three-dimensional curved surface generated based on the spline curve(s) drawn in the MPR window may be displayed in real time, and the volume rendering window or the mesh rendering window may synchronously display the spline curve(s) and the control point(s) that form the spline curve(s). The three-dimensional curved surface or the spline curve may be adjusted by adjusting the control point(s) in the three-dimensional curved surface.

In 920, whether to continue editing may be determined. Operation 920 may be performed by the judgment unit 414. If it is determined to continue to edit the control point(s), then the process 900 may return to 912, and relevant operation(s) may be repeated. Otherwise, operation 922 may be performed. In some embodiments, whether to continue to edit the control point(s) may be determined based on whether the curved surface displayed in the volume rendering window satisfies user requirement(s) or one or more pre-determined conditions. The pre-determined condition(s) may include whether the curved surface includes at least a portion of blood vessels, calcified tissue, injured tissue, etc. In some embodiments, the judgment unit 414 may determine whether the curved surface satisfies the pre-determined condition(s) based on characteristic information of the curved surface. For example, the judgment unit 414 may determine whether the gray level of all the pixels or voxels in the curved surface is less than a pre-determined gray level threshold. If the gray level of all the pixels or voxels is less than the pre-determined threshold, then the curved surface may not satisfy the pre-determined condition. If the gray level of at least a portion of the pixels or voxels is greater than the pre-determined gray level threshold, then the curved surface may satisfy the pre-determined condition.

In 922, the cured surface may be generated based on the edited spline curve. Operation 922 may be performed by the curved surface generation unit 408. In some embodiments, the curved surface may be generated based on an interpolation algorithm in 922.

It should be noted that the above descriptions of the process 900 for generating a curved surface are only for the convenience of illustration, and not intended to limit the present disclosure to the scope of the exemplary embodiments. It should be understand that for those skilled in the art, after understanding the principles of the present disclosure, various modifications may be conducted to the process 900 for generating a curved surface without departing from the principles. For example, generating the curved surface and/or editing operation may include acquiring image data. As another example, generating the curved surface and/or editing operation may further include pre-processing the image data. Similar variations fall within the protection scope of the present disclosure.

Figure 10B:
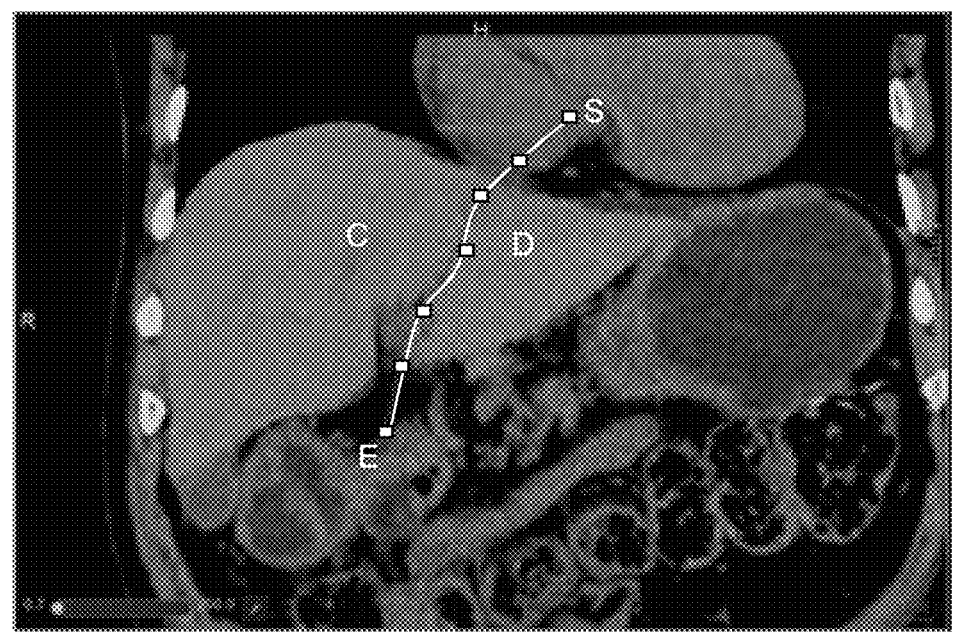

FIGS. 10A and 10B are schematic diagrams of an exemplary spline curve according to some embodiments of the present disclosure. FIG. 10A is a two-dimensional slice image of liver tissue in a traverse plane. The spline curve SE may segment the liver region into A and B portions in the slice image in the traverse plane. A segmentation curved surface for the liver may be generated based on spline curves in a two-dimensional slice image sequence in the traverse plane, wherein the curved surface may segment the liver tissue into front and back portions. FIG. 10B is a two-dimensional slice image of liver tissue in a sagittal plane. The spline curve SE segments the liver region into C and D portions in the two-dimensional slice image in the sagittal plane. The segmentation curved surface for the liver may be generated based on the spline curves in a plurality of two-dimensional slice images in the sagittal plane, wherein the curved surface may segment the liver tissue into top and bottom portions.

Figure 11:
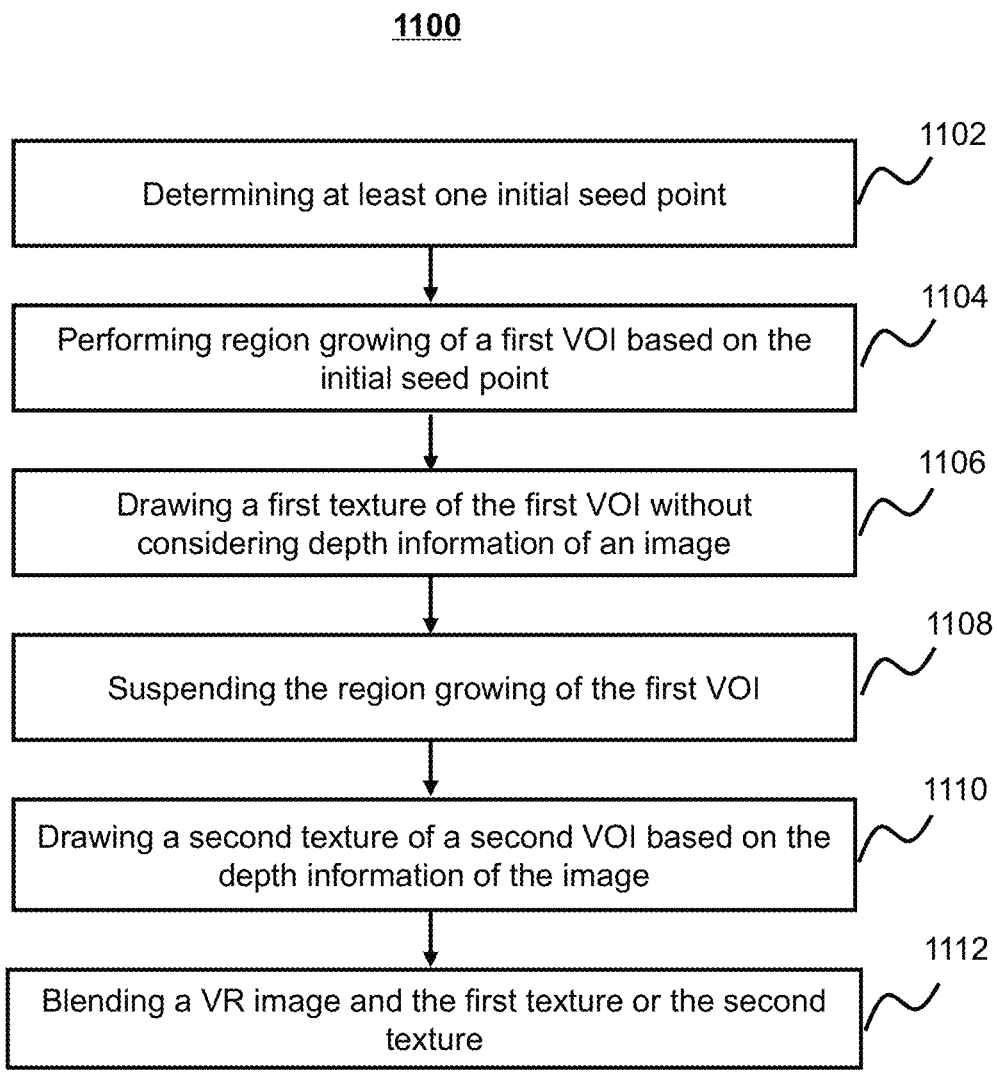
FIG. 11 is a flowchart of an exemplary process for performing region growing on a VOI based on volume rendering (VR) according to some embodiments of the present disclosure.

FIG. 11 is a flowchart of an exemplary process for performing region growing on a VOI based on volume rendering (VR) according to some embodiments of the present disclosure. In some embodiments, the operation 653 of segmenting a VOI based on a region growing algorithm in the process 650 may be implemented according to the process 1100 illustrated in FIG. 11. In 1102, at least one initial seed point may be determined. In some embodiments, operation 1102 may be performed by the VOI generation unit 404. In some embodiments, the initial seed point may include at least one voxel. In some embodiments, the initial seed point may be a region, and the region may include a set of a plurality of voxels. In some embodiments, the selection of the initial seed point may be performed based on a VR image or image data (e.g., a two-dimensional slice image).

In some embodiments, the initial seed point may be determined manually. For example, a user may select the initial seed point via the interactive device 140 (e.g., a mouse). In some embodiments, the initial seed point may be selected automatically. For example, the initial seed point may be the voxels or pixels having the largest probability of appearance in the gray level histogram of the image. As another example, the initial seed point may be the center point of the image. In some embodiments, the image may be segmented based on one or more of the image segmentation algorithms described in the present disclosure, and then the seed point may be selected based on the segmented image. For instance, the initial seed point may be determined based on a watershed segmentation algorithm. In some embodiments, the image may be segmented into a plurality of rectangular regions, and the center point of each rectangular region may be used as an initial seed point. For example, an edge detection may be performed on the image, and the center point of an adjacent boundary region, any point in a closed region detected by the edge detection, or a local minimum value point may be selected as the initial seed point. As another example, a gray level gradient image may be obtained using a mathematical morphology algorithm, and then the initial seed point may be selected in the regions with relatively small and/or large change(s) in the gray level gradient image.

In some embodiments, the initial seed point may be selected based on one or more selection standards in operation 1102. The selection standard(s) may include the similarity of the characteristics of the initial seed point and the characteristics of adjacent pixels or voxels. The characteristics may include gray level values, colors, texture, luminance, or the like, or any combination thereof. The selection standard(s) may include a similarity function, a spectral angel, a spectral distance, a normalizing vector distance, etc. The similarity function may be used to measure the similarity of the characteristics of two voxels, such as a similarity coefficient value function, a distance function, etc. The similarity coefficient value function may be used to measure the similarity of two voxels based on a similarity coefficient value. The similarity coefficient value may be relatively large if the two voxels are similar; the similarity coefficient value may be relatively small if the two voxels are less similar. In a distance function, each voxel may be considered as a point in a high-dimensional (e.g., four-dimensional or higher) space, and then a certain distance (e.g., Mahalanobis distance, Euclidean distance, etc.) may be used to represent the similarity between the voxels. The properties of the voxels may be relatively similar if the distance is relatively close; the voxels may be relatively different if the distance is relatively far. If the spectral data are considered as vectors in a multi-dimensional space, the spectral angle may refer to the angle between the vector pixels or voxels and adjacent vector pixels or voxels. The spectral angle of adjacent voxels may be used to measure the spectral difference between the adjacent voxels. If the spectral data are considered as vectors in a multi-dimensional space, the spectral distance may refer to the distance between the vector pixels or voxels and adjacent vector pixels or voxels. The normalizing vector distance may define the spectral difference between two voxels with a comprehensive consideration of the spectral angle and the spectral distance; the smaller the spectral difference is, the higher the possibility for the voxel to be selected as the seed point may be; the bigger the spectral difference is, the lower the possibility for the voxel to be selected as the seed point may be.

In 1104, region growing of a first VOI may be performed based on the at least one initial seed point. In some embodiments, operation 1104 may be performed by the VOI generation unit 404. In some embodiments, region growing of the first VOI may be performed based on one or more growing criteria, each voxel in a neighborhood of an initial seed point may be traversed, and the region where the voxel(s) that meet the growing criteria are located may be combined with the region where the initial seed point is located. In some embodiments, the newly added voxel(s) may be used as the seed point(s) for a next round of region growing, and the region growing may be continued until no pixel that satisfies the growing criteria may be found. In some embodiments, the growing criteria may relate to characteristics of voxels, such as texture, gray level, colors, luminance, or the like, or any combination thereof. For instance, if the growing criteria relate to the gray level of voxels, the absolute value of the difference in the gray level values of the seed point and a neighborhood voxel is less than a pre-determined threshold, then the region where the voxel is located and the region where the seed point is located may be combined. As another example, if the growing criteria relate to the similarity of texture characteristics, specifically, the mean value (e.g., contrast, correlation and entropy, etc.) of the texture characteristic values of voxels in the neighborhood of the seed point may be determined based on a gray level co-occurrence matrix, the mean value is compared with the texture characteristic values of voxels in the region where the seed point is located, and the difference of the mean value of the texture characteristic values of voxels in the neighborhood of the seed point and the texture characteristic values of voxels in the region where the seed point is located is less than a pre-determined threshold, then the voxels in the neighborhood of the seed point may be combined into the region where the seed point is located.

In some embodiments, the region growing may be performed based on image data. The image data may be volume data (e.g., a plurality of two-dimensional slice image sequences). The VOI grown based on image data may be used for the reconstruction and display of a VR image of the VOI region based on a volume rendering technique. For instance, a virtual projection line may pass through the VOI region of two-dimensional slice image sequence(s) at a pre-determined angle, a two-dimensional projection may be performed on voxels in different slice images on the same projection line, then the voxels in different slice images may be comprehensively displayed based on a virtual illumination effect. In some embodiments, the region growing may be performed based on a VR image. For instance, the initial seed point may be selected based on a VR image, the region growing may be performed, and then the generated VOI region may be displayed in different pseudo colors.

In 1106, a first texture of the first VOI may be drawn without considering depth information of an image. In some embodiments, operation 1106 may be performed by the VOI generation unit 404. In some embodiments, the VR image may include the first VOI and a background region. In some embodiments, the depth information may include three-dimensional space information of voxels or pixels. The depth information may be used to represent the location of the voxels or pixels on the projection line that passes through the voxels or pixels, or the distance between the voxels or pixels and the projection plane. In some embodiments, in operation 1106, if a two-dimensional projection of the three-dimensional coordinates of all the voxels in the first VOI is performed, a portion of the voxels on the projection line that belongs to the background region or have lower transparency than the voxels in the first VOI may not be considered. In some embodiments, the first VOI may be a region including all the voxels extracted based on the current region growing. In some embodiments, the first VOI may be a region including newly added voxels extracted based on the current region growing that is performed based on the previous region growing. The first texture of the first VOI may be represented by the gray level distribution of the voxels in the VOI and neighborhood voxels thereof. The first texture of the first VOI may illustrate the spatial color distribution and/or light intensity distribution of the voxels in the first VOI.

In some embodiments, the first texture of the first VOI may be drawn based on one or more texture extraction techniques. The texture extraction techniques may include a statistics algorithm, a geometric algorithm, a model algorithm, a signal processing algorithm, a structure algorithm, or the like, or any combination thereof. The statistics algorithm may perform texture statistics in a region based on the gray level characteristics of the voxels and the neighborhood voxels, such as a gray-level co-occurrence matrix (GLCM) algorithm, a gray-gradient co-occurrence matrix algorithm, swim-matrices statistics algorithm, a gray level differential statistics algorithm, a crossed diagonal matrix algorithm, a self-correlation function algorithm, a semi-variogram algorithm, etc. The geometric algorithm may extract the texture based on that the texture of the voxels if formed by arranging a plurality of voxels under a certain rule, such as a Voronio checkerboard characteristics algorithm. The model algorithm may extract the texture based on that the texture of the voxels is formed by a certain distribution model, wherein the distribution model may be controlled by parameters. An exemplary model algorithm may include a random model algorithm, a fractal model algorithm, a complex network model algorithm, a mosaic model algorithm, etc. A typical model algorithm may include a random model algorithm, such as a Markov Random Field (MRF) model algorithm, a Gibbs random model algorithm, a moving average model algorithm, a simultaneous autoregressive model algorithm, an autoregressive sliding model algorithm, a generalized correlation model algorithm, etc. Based on a spatial domain, a transformation domain and/or a multi-scale analysis, the signal processing algorithm may perform a correlation transformation on a region of the image and then extract relatively stable characteristic values, and represent the consistency in the region and the difference between regions using the characteristic values. The signal processing algorithm may be performed based on a transformation algorithm, a filtering algorithm, a Laws texture measurement algorithm, or the like, or any combination thereof. The transformation algorithm may include a Radom transformation algorithm, a local Fourier transformation algorithm, a local Walsh transformation algorithm, a Gabor transformation algorithm, a wavelet transformation algorithm, a hadamard transformation algorithm, a discrete cosine transformation algorithm, etc. The filtering algorithm may include a characteristic filtering algorithm, a quadrature mirror filtering algorithm, an optimized finite impulse response (FIR) filtering algorithm, etc. The structure algorithm may extract texture characteristics based on the type and number of the texture elements, the repetitive spatial organization structure among the elements, and/or the arrangement rule, such as a syntax texture analysis algorithm, a mathematical morphology algorithm, etc.

In 1108, the region growing of the first VOI may be suspended. In some embodiments, operation 1108 may be performed by the VOI generation unit 404. In some embodiments, a user may input an instruction for suspending the region growing via the interactive device 140 (e.g., a mouse, a keyboard, etc.), and the VOI generation unit 404 may receive the instruction and suspend the region growing. In some embodiments, the region growing may be suspended by interactive operations such as rotating, translating, and/or scaling the operation interface, etc. In some embodiments, the region growing may be suspended by an operation of releasing the mouse.

In 1110, a second texture of a second VOI may be drawn based on depth information of the image. In some embodiments, operation 1110 may be performed by the VOI generation unit 404. In some embodiments, the depth information of voxels may be extracted based on image data to obtain the depth information of the voxels in operation 1110. The extraction of the depth information may be performed based on one or more depth information extraction techniques. The depth information extraction technique(s) may include multi-view stereo algorithm, a photometric stereo vision algorithm, a defocusing inference algorithm, an algorithm based on machine learning, or the like, or any combination thereof. The multi-view stereo algorithm may extract pixels based on two-dimensional images, match the voxels with angle images thereof, and then determine three-dimensional coordinates of the voxels based on the matched voxels. The photometric stereo vision algorithm may estimate one or more VOI surface normal vectors based on image sequence(s) under different illumination conditions, obtain the three-dimensional coordinates of the final voxels using techniques such as a line integral algorithm, and obtain depth information of the voxels. The defocusing inference algorithm may reckon the depth information of voxels based on the fuzzy extent of the VOI. The algorithm based on machine learning may include using a Markov Random Field model as a model for machine learning, and performing supervised learning. In some embodiments, the drawing of the second texture of the second VOI may be performed according to one or more texture extraction algorithms described in the present disclosure.

In some embodiments, the first VOI may include a first voxel set, and the second VOI may include a second voxel set. In some embodiments, the first voxel set may include the second voxel set. In some embodiments, the second VOI may be determined based on the depth information of voxels in the first voxel set and/or the transparency of voxels in a VR image. For example, a projection line passing through one voxel of the first voxel set may be used to pass the VR image at a pre-determined angle. On the projection line between the voxel and the projection plane, if no other voxel that has higher transparency than the voxel is present, then the voxel may belong to the second VOI region; if another voxel that has higher transparency than the voxel is present on the projection line between the voxel and the projection plane, then the voxel may not belong to the second VOI region.

In 1112, the VR image may be blended with the first texture of the first VOI or the second texture of the second VOI. In some embodiments, operation 1112 may be performed by the VOI generation unit 404. In some embodiments, after the VR image and the first texture of the first VOI are blended, the first VOI may be displayed in the VR image in operation 1112. The first VOI may include voxels newly added during the process of region growing (i.e., the voxels newly added in the current region growing compared with previous region growing) or all the voxels generated during the process from the original region growing to the current region growing. In some embodiments, after the VR image and the second texture of the second VOI are blended, the second VOI may be displayed in the VR image in operation 1112. For instance, during the extraction process of blood vessel tissue of head and neck, the blood vessel tissue may be the first VOI, a portion of the blood vessel tissue that is not masked by the skull may be the second VOI. The first VOI and the VR image of head and neck may be blended for presenting the changing process of the blood vessel tissue (e.g., whether the growing of blood vessel tissue is overflowed, incomplete or not). The second VOI and the VR image of the head and neck may be blended for presenting the shadowing relationship of the blood vessel tissue and tissue such as the skull, etc.

It should be noted that the above descriptions of the process 1100 are only for the convenience of illustration, and not intended to limit the present disclosure to the scope of the exemplary embodiments. It should be understand that for those skilled in the art, after understanding the principles of the present disclosure, various modifications may be conducted to the process 1100 without departing from the principles. For example, the process 1100 may further include pre-processing the image data. As another example, operation 1108 and/or 1110 may be omitted from the process 1100. As a further example, the growth status of region growing may be displayed in real time in a VR display window and/or an MPR display window. Similar variations fall within the protection scope of the present disclosure.

Figure 12:
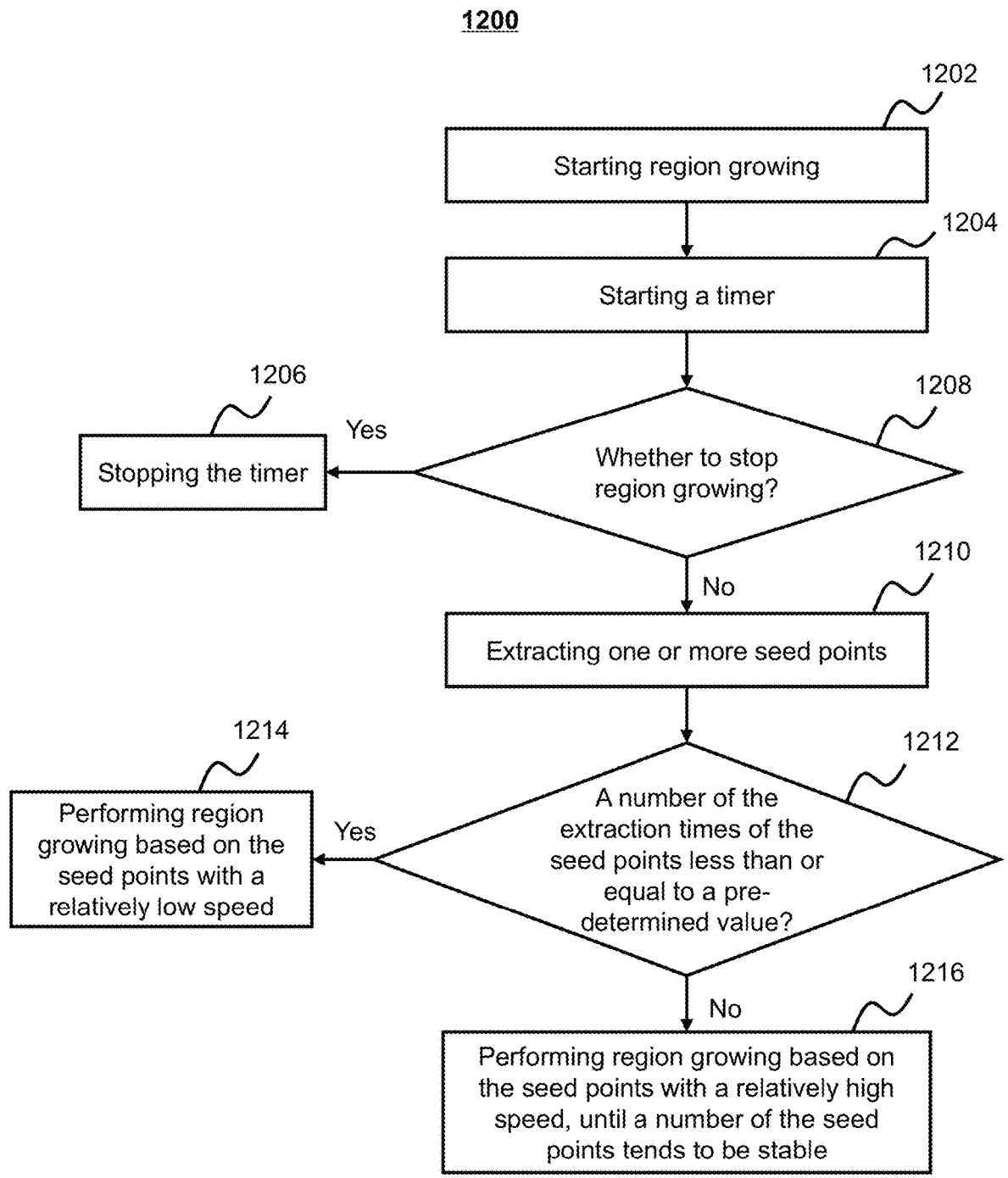
FIG. 12 is a flowchart of an exemplary process for non-linear VOI region growing according to some embodiments of the present disclosure.

FIG. 12 is a flowchart of an exemplary process for non-linear VOI region growing according to some embodiments of the present disclosure. In some embodiments, the operation 1104 of performing region growing on the first VOI in the process 1100 may be implemented according to the process 1200 as illustrated in FIG. 12. In operation 1202, region growing may be started. In some embodiments, operation 1202 may be implemented by the VOI generation unit 404. In some embodiments, a user may input an instruction of starting the region growing via the interactive device 140, and the VOI generation unit 404 may initiate the region growing based on the instruction inputted by the user. For example, a user may click on the image region using a mouse to initiate (or start) the region growing. As another example, a user may click an initiation button or a starting button in the operation interface to initiate (or start) the region growing.

In 1204, a timer may be started. The operation 1204 may be performed by the VOI generation unit 404. In some embodiments, the VOI generation unit 404 may start the timer at the time when the region growing is started or after a time interval. In some embodiments, the timer may be started at the time when the region growing is started in the operation 1202. For instance, when a user clicks on an image region and starts the region growing, the timer may be simultaneously started. In some embodiments, after the region growing is started, the timer may be automatically started after a pre-determined first time interval. The first time interval may be pre-determined based on the size of the VOI region. For instance, if the VOI region is relatively small, then the first time interval may be relatively short; if the VOI region is relatively large, then the first time interval may be relatively long.

In 1208, whether to stop region growing may be determined. In some embodiments, operation 1208 may be performed by the judgment unit 414. In some embodiments, the stop of the region growing may include a termination or a suspension of the region growing. In some embodiments, whether a condition is satisfied for terminating the region growing or not may be determined in 1208. The condition for terminating the region growing may include terminating the region growing if no further voxel satisfies the growing criteria. More descriptions of the growing criteria may be found elsewhere in the present disclosure (e.g., FIG. 11 and descriptions thereof). In some embodiments, whether to suspend the region growing or not may be determined based on user interactive information in 1208. For instance, the region growing may be suspended if a user performs an operation such as releasing a mouse and/or translating, rotating, or scaling the operation interface, etc. If the region growing is not stopped, an operation 1210 of extracting seed points may be performed; if the region growing is stopped, an operation 1206 of stopping the timer may be performed. In some embodiments, the timer may record the frequency of extraction of seed points. For example, the times of the operation of the timer may represent the times of the extraction of the seed points.

In 1210, the times of extracting the seed points may be determined based on the timer. In some embodiments, the extraction times of the seed points may be determined in a pre-determined second time interval after the timer is started. The second time interval may be set based on the size of the VOI region. For instance, if the VOI region is relatively small, then the second time interval may be relatively short; if the VOI region is relatively large, then the second time interval may be relatively long.

In 1212, whether the number of the extraction times of the seed points is less than or equal to a pre-determined threshold may be determined. If the number of the extraction times of the seed points is less than or equal to the pre-determined threshold, then 1214 may be performed; if the number of the extraction times of the seed points is greater than the pre-determined threshold, then 1216 may be performed. In some embodiments, the pre-determined threshold may be set based on the size of the VOI region. For instance, if the VOI region is relatively small, then the pre-determined threshold may be relatively small; if the VOI region is relatively large, then the pre-determined threshold may be relatively large. In some embodiments, the pre-determined threshold may range from 1 to 5. For example, the pre-determined threshold may be 5. In some embodiments, the pre-determined threshold may range from 1 to 10. It should be noted that, the above mentioned values for the pre-determined threshold are only provided for the convenience of description, and may not limit the present disclosure to the scope of the embodiments.

In 1214, the region growing may be performed based on the seed points with a relatively low speed. In some embodiments, in the operation 1214, the growing speed of the seed points may be decreased during the time interval of the current extraction of seed points and the next extraction of seed points, so as to decrease the number of the grown seed points. For instance, if the VOI region is relatively small, a user may desire to observe the status of the VOI region growing, and then a small number of seed points may be grown with a relatively low speed to control the VOI region and prevent the seed points from growing too fast.

In 1216, the region growing may be performed based on the seed points with a relatively high speed, and the speed may be increasing until the number of the seed points tends to be stable. In some embodiments, in the operation 1216, the growing speed of the seed points may be increased during the time interval of the current extraction of seed points and the next extraction of seed points, so as to increase the number of the grown seed points. For instance, if the VOI region is relatively large, a user may desire that the speed of the region growing is relatively high during the early stage of the VOI region growing; however, during the late stage of the VOI region growing, the growing may easily overflow due to the large number of seed points, and thus the speed of the region growing may need to be decreased. The growing speed may be adjusted based on the operation times of the timer determined in 1210. Therefore, in the early stage of region growing, the growing speed of the seed points may be increased to increase the amount of the grown seed points, so as to increase the speed of region growing. In the late stage of the region growing, the growing speed of the seed points may be decreased to make the amount of the grown seed points tend to be stable, so as to decrease the speed of region growing. It should be noted that a low speed and a high speed is relative. For instance, a speed lower than a pre-determined value may be considered as a relatively low speed, while a speed higher than the pre-determined value may be considered as a relatively high speed. Similarly, a small number of seed points and a large number of seed points may also be relative. For example, a number of seed points less than a pre-determined number may be considered as a small number of seed points, while a number of seed points greater than the pre-determined number may be considered as a large number of seed points.

It should be noted that the above descriptions of the process 1200 for non-linear VOI region growing are only for the convenience of illustration, and not intended to limit the present disclosure to the scope of the exemplary embodiments. It should be understand that for those skilled in the art, after understanding the principles of the present disclosure, various modifications may be conducted to the process 1200 for non-linear VOI region growing without departing from the principles. For example, the process 1200 for non-linear VOI region growing may include selecting initial seed points. As another example, the process 1200 for non-linear VOI region growing may include suspending region growing, rending image(s), displaying image(s), etc. As a further example, the status of region growing may be displayed in real time in a VR display window or an MPR display window. Similar variations fall within the protection scope of the present disclosure.

Figure 13:
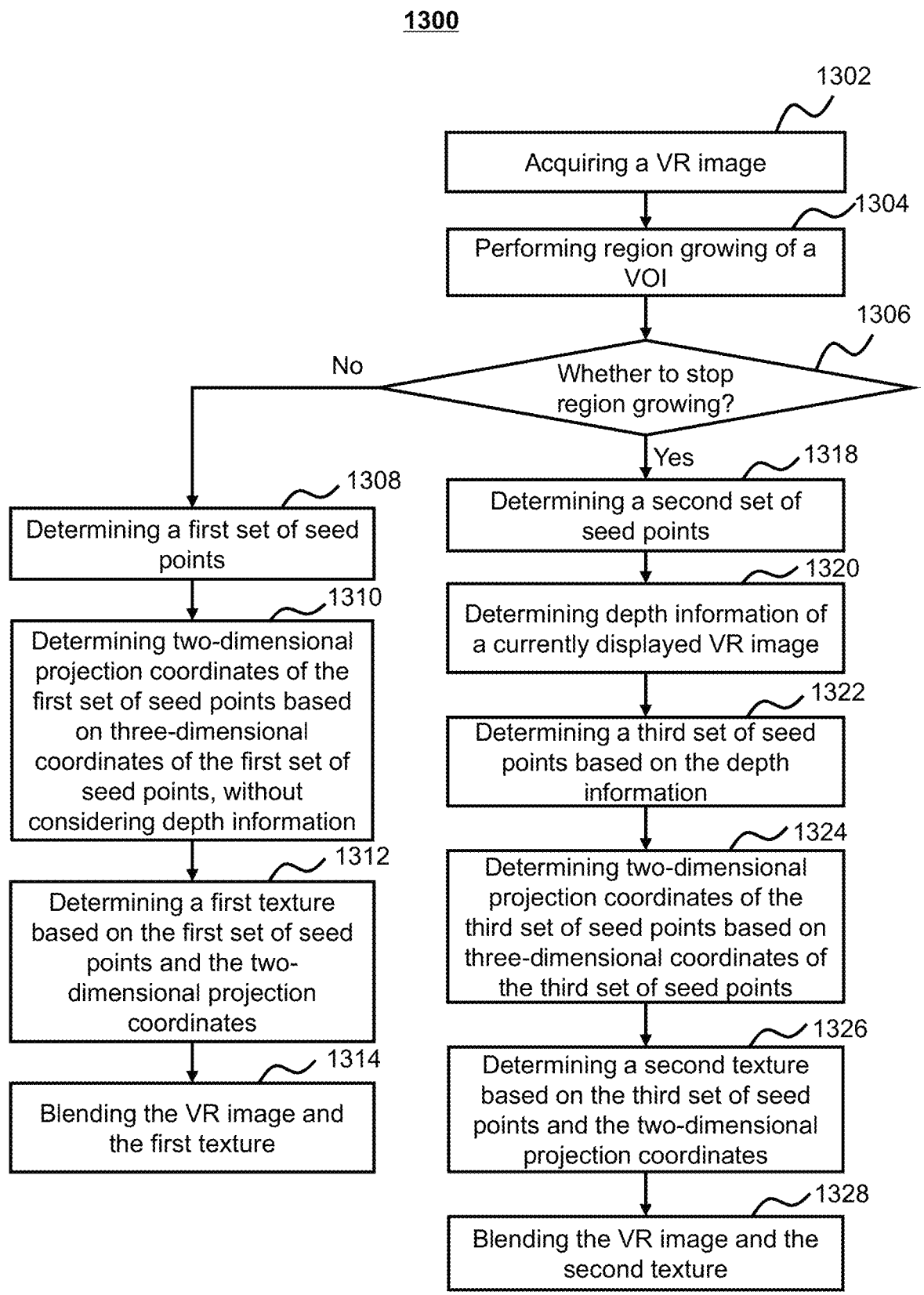
FIG. 13 is a flowchart of an exemplary process for determining a VOI based on a VR image according to some embodiments of the present disclosure.

FIG. 13 is a flowchart of an exemplary process for determining a VOI based on a VR image according to some embodiments of the present disclosure. The process 1300 may be an exemplary embodiment of the process 1100.

In 1302, a VR image may be acquired. In some embodiments, operation 1302 may be performed by the image data acquisition module 302. In some embodiments, the VR image may be acquired by reconstructing the VR image based on image data using a volume rendering technique. In some embodiments, the VR image may include at least one VOI and/or background region.

In 1304, region growing of a VOI may be performed. In some embodiments, operation 1304 may be performed by the VOI generation unit 404. In some embodiments, the determination of the VOI may include a plurality of processes of region growing, and similar or the same voxels may be extracted in each process of region growing. In some embodiments, the region growing may include selecting an initial seed point. The initial seed point may be selected manually or automatically. More descriptions of the selection of the initial seed point may be found elsewhere in the present disclosure (e.g., FIG. 11 and descriptions thereof). The initial seed point may be selected based on voxel texture characteristics. In some embodiments, neighborhood voxels of the initial seed point may be traversed to select voxels that satisfy pre-determined growing criteria in 1304. The voxels that satisfy the pre-determined growing criteria may be combined with the initial seed point into a same region, i.e., the VOI region. Newly added voxels in the VOI may serve as new seed points for next region growing (i.e., extracting similar or the same voxels in the next growing).

In 1306, whether to stop region growing may be determined. In some embodiments, operation 1306 may be performed by the VOI generation unit 404. In some embodiments, a current operation mode may be determined, and whether to stop region growing may be determined based on the current operation mode in 1306. In some embodiments, the current operation mode may include the operational action by a user, for instance, clicking a mouse, releasing a mouse, translating, rotating, or scaling the operation interface, etc. In some embodiments, if the user performs an operational action such as clicking a mouse, inputting an instruction of starting or keeping a mouse as unreleased, etc., 1308 may be performed.

In 1308, a first set of seed points may be determined. In some embodiments, operation 1308 may be performed by the VOI generation unit 404. The first set of seed points may include at least one of first voxels. The first voxels may include at least one voxel newly added in the process of the current region growing relative to the process of the previous region growing. For instance, the VOI generation unit 404 may start (or resume after a previous growing suspension) performing a VOI region growing at a first time point, and suspend the VOI region growing at a second time point. Thus the first set of seed points may include the seed points growing from the first time point to the second time point. In some embodiments, the newly added voxels may represent a real-time changing status of the VOI growing. In some embodiments, the current region growing may include a process of generating/extracting seed points at a time closest to but before the time point of suspending the region growing.

In 1310, two-dimensional projection coordinates of the first set of seed points may be determined based on three-dimensional coordinates of the first set of seed points, without considering depth information. In some embodiments, operation 1310 may be performed by the VOI generation unit 404. In some embodiments, a projection line may pass through the first voxels at a certain angle, and the first voxels may project on a projection plane (i.e., a display plane) to generate two-dimensional projection coordinates. In some embodiments, when a two-dimensional projection is performed on the first voxels, voxels in the background region on the projection line passing from the first voxels to the projection plane, or voxels that have a lower transparency value than the first voxels may not be considered. In some embodiments, a transparency value lower than the transparency value of the first voxels may be set as a maximum value (or the opaqueness may be set as 0). For example, if region growing is performed on blood vessel tissue of head and neck based on volume rendering (VR) images of head and neck, a portion of the blood vessel tissue may be masked by the skull. The first set of seed points may be blood vessel tissue growing in real time. If the depth information of the VR image of the head and neck is not considered, then the transparency of an image of the skull portion may be set as the maximum value. In other words, the growing status of the blood vessels may be displayed without considering the shadowing relationship of the blood vessel tissue and the skull.

In 1312, the first texture of the first set of seed points may be determined based on the first set of seed points and the two-dimensional projection coordinates. In some embodiments, operation 1312 may be performed by the VOI generation unit 404. In some embodiments, the first texture may be the texture of first voxels in the first set of seed points. In some embodiments, the texture of the first voxels within a region corresponding to the two-dimensional projection coordinates may be determined based on the two-dimensional projection coordinates. In some embodiments, the extraction of the texture characteristics may be performed based on one or more texture extraction techniques described in the present disclosure. In some embodiments, a texture extraction operation may be performed on the first set of seed points, and the extracted texture may be drawn and displayed in the corresponding region of the two-dimensional projection coordinates.

In 1314, the first texture and the VR image may be blended. In some embodiments, operation 1314 may be performed by the VOI generation unit 404. In some embodiments, the texture of the background region and the first texture may be blended in 1314. The texture of the background region may be extracted based on any texture extraction technique described in the present disclosure.

In 1318, a second set of seed points may be determined. In some embodiments, operation 1318 may be performed by the VOI generation unit 404. The second set of seed points may include at least one of second voxels. The second voxels may include all the voxels newly added from the beginning of the region growing to the suspension time point of the region growing. In some embodiments, the first set of seed points may include the second seed points.

In 1320, depth information of a currently displayed VR image may be determined. In some embodiments, operation 1320 may be performed by the VOI generation unit 404. In some embodiments, the currently displayed VR image may include a portion of the grown VOI. More descriptions of the determination of the depth information may be found elsewhere in the present disclosure (e.g., FIG. 11 and descriptions thereof). In some embodiments, the depth information of the VR image may include the depth information of voxels in the current VR image. In some embodiments, the depth information of voxels in the currently displayed VR image may be determined based on the current VR image in 1320. In some embodiments, the depth information of the voxels may be determined based on image data (e.g., a two-dimensional slice image sequence) in 1320.

In 1322, a third set of seed points may be determined based on the depth information. In some embodiments, operation 1322 may be performed by the VOI generation unit 404. The third set of seed points may include at least one of third voxels. In some embodiments, the third set of seed points may include at least a portion of the second set of seed points. For example, the VOI generation unit 404 may start to perform (or resume after a previous suspension) the region growing of the VOI at a first time point, suspend the region growing of the VOI at a second time point, and continue the region growing of the VOI at a third time point. Thus the third set of seed points may include at least a portion of the seed points grown from the first time point till the third time point. In some embodiments, the depth information may represent location information of different voxels in the three-dimensional space. In some embodiments, the third voxels and the third set of seed points may be determined based on the location information in the three-dimensional space and the transparency of different voxels. For example, a projection line may be used to pass through the VR image (e.g., the currently displayed VR image or the VR image acquired in 1302) at a pre-determined angle, and the projection line may pass through the second voxels in the second set of seed points. On the projection line from the location of a second voxel to the projection plane, if no voxel that has lower transparency than the second voxel is present, then the second voxel may be a third voxel in the third set of seed points. If a voxel that has lower transparency than the second voxel is present, then the second voxel may not be a third voxel in the third set of seed points.

In 1324, two-dimensional projection coordinates of the third set of seed points may be determined based on the three-dimensional coordinates thereof. In some embodiments, operation 1324 may be performed by the VOI generation unit 404. In some embodiments, a projection line may pass through the third voxel in the third set of seed points at a pre-determined angle, and the third voxel may be projected onto a projection plane (i.e., a display plane) and generate two-dimensional projection coordinates.

In 1326, a second texture of the third set of seed points may be determined based on the third set of seed points and the two-dimensional projection coordinates. In some embodiments, operation 1326 may be performed by the VOI generation unit 404. In some embodiments, the second texture may be the texture of the third voxels in the third set of seed points in the region corresponding to the two-dimensional coordinates. In some embodiments, the second texture may be extracted based on any texture extraction technique described in the present disclosure. In some embodiments, a texture extraction operation may be performed on the third set of seed points, and the extracted texture may be drawn and displayed in the corresponding region of the two-dimensional projection coordinates.

In 1328, the VR image and the second texture may be blended. In some embodiments, operation 1328 may be performed by the VOI generation unit 404. In some embodiments, the texture of the background region may be blended with the second texture. The texture of the background region may be extracted based on any texture extraction technique in the present disclosure.

It should be noted that the above descriptions of the process 1300 are only for the convenience of illustration, and not intended to limit the present disclosure to the scope of the exemplary embodiments. It should be understand that for those skilled in the art, after understanding the principles of the present disclosure, various modifications may be conducted to the process 1300 without departing from the principles. For example, the process 1300 may include acquiring image data. As another example, the process 1300 may further include pre-processing the image data. Similar variations fall within the protection scope of the present disclosure.

Having thus described the basic concepts, it may be rather apparent to those skilled in the art that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Furthermore, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely by hardware, entirely by software (including firmware, resident software, micro-code, etc.) or combining software and hardware implementation that may all generally be referred to herein as a "block," "module," "engine," "unit," "component," or "system." Moreover, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the operator's computer, partly on the operator's computer, as a stand-alone software package, partly on the operator's computer and partly on a remote computer or entirely on the remote computer or server. In the latter scenario, the remote computer may be connected to the operator's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the disclosure are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to the embodiments precisely shown and described in the present application.

What is claimed is:

1. A method implemented on at least one machine, each of the at least one machine having at least one processor and one storage, the method comprising:
   acquiring image data generated by a medical imaging device;
   performing region growing of a volume of interest (VOI);
   suspending the region growing of the VOI;
   determining a texture of the VOI based on voxels in a current volume rendering (VR) image, wherein on a projection line passing through the current VR image at an angle and one of the voxels, no other voxel that has higher transparency than the voxel is present,
   determining a first set of seed points, the first set of seed points including all seed points growing from a first point in time to a second point in time when the region growing is suspended;
   determining depth information of the current VR image;
   determining a second set of seed points based on the depth information, wherein the first set of seed points includes the second set of seed points;
   determining, based on a plurality of three-dimensional coordinates of the second set of seed points, a plurality of two-dimensional projection coordinates of the second set of seed points; and
   determining based on the plurality of two-dimensional projection coordinates of the second set of seed points, at least one portion of the VOI, voxels in a current VOI image including the second set of seed points, wherein the depth information represents location information of different voxels in a three-dimensional space and the second set of seed points are determined based on the location information in the three-dimensional space and a transparency of the different voxels, on a projection line passing through the current VR image at an angle and a first voxel in the first set of seed points,
   if no other voxel that has higher transparency than the first voxel is present, the first voxel belongs to the second set of seed points, or
   if a voxel that has higher transparency than the first voxel is present, the first voxel does not belong to the second set of seed points.

2. The method of claim 1, wherein the at least one portion of the VOI includes at least one voxel, and a depth relating to the voxel is less than or equal to a depth relating to the image data.

3. The method of claim 1, wherein the region growing of the VOI is suspended according to a user instruction indicating an interactive operation including at least one of rotating, translating, or scaling.

4. The method of claim 1, wherein the second set of seed points includes at least a portion of seed points grown from the first time point till a third time point after the second time point, and a depth relating to the second set of seed points is less than or equal to a depth relating to the image data.

5. A method implemented on at least one machine, each of the at least one machine having at least one processor and one storage, the method comprising:
   acquiring image data generated by a medical imaging device;
   performing region growing of a volume of interest (VOI);
   determining whether the region growing of the VOI is stopped; and
   determining a texture of the VOI based on a determination result including:
   in response to determining that the region growing of the VOI is not stopped, determining a texture of the VOI without considering depth information of the image data including; or
   in response to determining that the region growing of the VOI is stopped, determining the texture of the VOI with considering depth information of the image data including:
   determining a first set of seed points, the first set of seed points including all seed points growing from a first point in time to a second point in time when the region growing is suspended;
   determining depth information of a current volume rendering (VR) image;
   determining a second set of seed points based on the depth information, wherein the first set of seed points includes the second set of seed points;
   determining, based on a plurality of three-dimensional coordinates of the second set of seed points, a plurality of two-dimensional projection coordinates of the second set of seed points; and
   determining based on the plurality of two-dimensional projection coordinates of the second set of seed points, at least one portion of the VOI, voxels in a current VOI image including the second set of seed points, wherein the depth information represents location information of different voxels in a three-dimensional space and the second set of seed points are determined based on the location information in the three-dimensional space and a transparency of the different voxels, on a projection line passing through the current VR image at an angle and a first voxel in the first set of seed points,
if no other voxel that has higher transparency than the first voxel is present, the first voxel belongs to the second set of seed points, or
if a voxel that has higher transparency than the first voxel is present, the first voxel does not belong to the second set of seed points.

6. The method of claim 5, wherein the determining a texture of the VOI without considering depth information of the image data includes:
determining the texture of the VOI based on voxels that do not belong to a background region or have transparency higher than other voxels in the VOI.

* * * * *